United States Patent [19]
Peyman et al.

[11] Patent Number: 5,696,248
[45] Date of Patent: Dec. 9, 1997

[54] 3'-MODIFIED OLIGONUCLEOTIDE DERIVATIVES

[75] Inventors: Anuschirwan Peyman, Kelkheim; Eugen Uhlmann, Glashütten; Carolin Carolus, Frankfurt, all of Germany

[73] Assignee: Hoechst Aktiengesellschaft, Frankfurt, Germany

[21] Appl. No.: 462,305

[22] Filed: Jun. 5, 1995

[30] Foreign Application Priority Data

Jun. 15, 1994 [DE] Germany .......................... 44 20 737.9
Jul. 9, 1994 [DE] Germany .......................... 44 24 263.8

[51] Int. Cl.$^6$ .......................... C07H 19/00; C07H 21/02; C12Q 1/68; A01N 43/04
[52] U.S. Cl. .......................... 536/22.1; 514/44; 536/23.1; 536/24.2; 435/6
[58] Field of Search .................. 536/22.1, 23.1, 536/24.2; 514/44; 435/6

[56] References Cited

FOREIGN PATENT DOCUMENTS 0552766  7/1993  European Pat. Off. .
0552767  7/1993  European Pat. Off. .

OTHER PUBLICATIONS

Wilk et al., Nucl. Acids Res., 18(8):2065–2068 (1990), "Backbone-modified oligonucleotides containing a butanediol-1,3 moiety as a 'vicarious segment' for the deoxyribosyl moiety-synthesis and enzyme studies".

(List continued on next page.)

*Primary Examiner*—Ardin H. Marschel
*Assistant Examiner*—Jezia Riley
*Attorney, Agent, or Firm*—T. Helen Payne; Raymond R. Wittekind

[57]  ABSTRACT

Novel oligonucleotide analogs of the formulae I and II

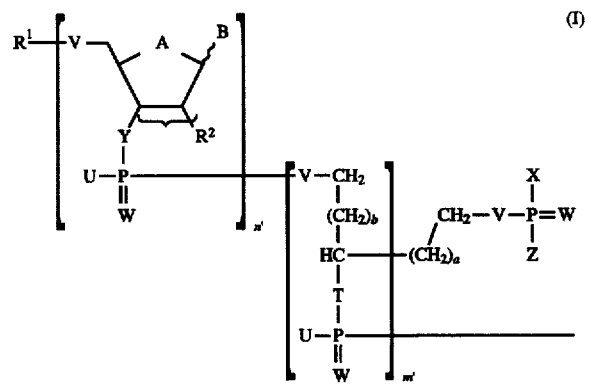

(I)

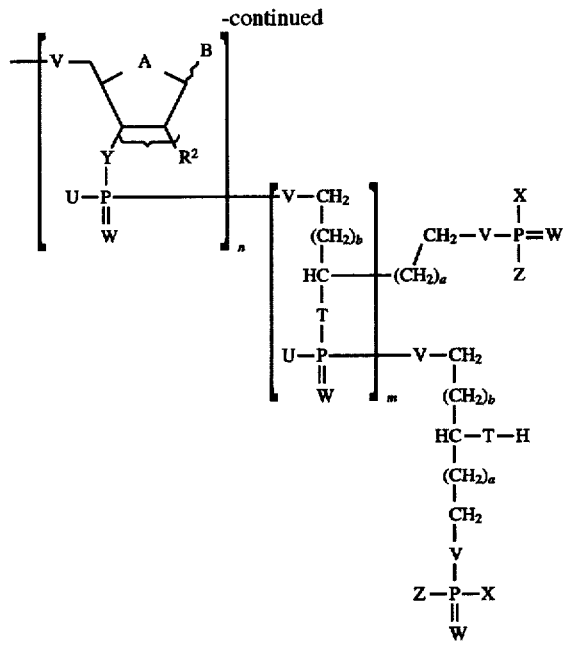

(II)

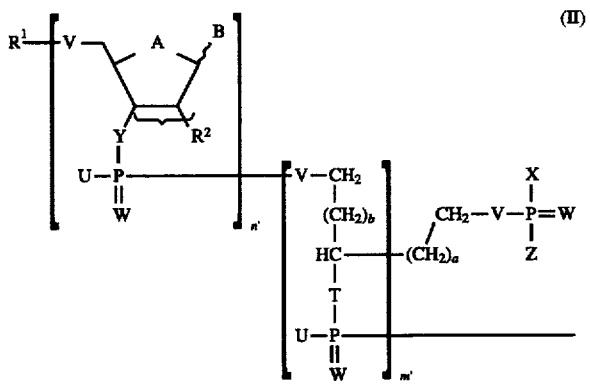

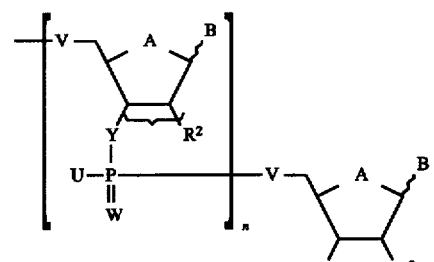

in which A, B, D, $R^1$, $R^2$, T, U, V, W, X, Y, Z, a, b, m, m', n and n' have the meanings stated in the description, with valuable physical, biological and pharmacological properties, and a process for the preparation thereof are described. Application thereof relates to the use as inhibitors of gene expression (antisense oligonucleotides, ribozymes, sense oligonucleotides and triplex forming oligonucleotides), as probes for detecting nucleic acids and as aids in molecular biology.

21 Claims, No Drawings

OTHER PUBLICATIONS

Seela et al., Nucl. Acids Res., 15(7):3113–3129 (1987), "Oligodeoxyribonucleotides containing 1,3–propanediol as nucleoside substitute".

Torrence et al., PNAS USA, 90:1300–1304 (1993), "Targeting RNA for degradation with a (2'–5')oligoadenylate–antisense chimera".

Vesnaver et al., PNAS USA, 86:3614–3618 (1989), "Influence of abasic and anucleosidic on the stability, conformation, and melting behavior of a DNA duplex: Correlations of thermodynamic and structural data".

Richardson et al., J. Am. Chem. Soc., 113:5109–5111 (1991), "Tethered Oligonucleotide Probes. A Strategy for the Recognition of Structured RNA".

De Vos et al., Nucleosides & Nucleotides, 13(10):2245–2265 (1994), "New Non Nucleosidic Phosphoramidites for the Solid Phase Multi–Labelling of Oligonucleotides: Comb–and Multifork–Like Structures".

Stein et al. "Antisense Oligonucleotides as Therapeutic Agents–Is the Bullet Really Magical?" Science vol. 261 pp. 1004–1011, 1993.

J. F. Milligan, et al., Journal of Medicinal Chemistry, 36, 1923 to 1937 (1993) published in the United States of America and entitled "Current Concepts in Antisense Drug Design".

M. Manoharan, "Antisense Research and Applications", Crooke and Lebleu, Editors, Chapter 17, CRC Press, Boca Raton, FL 1993, pp. 303 to 349;.

S. L. Beaucage, et al., Tetrahedron 49, 1925 to 1963 (1993) published in Great Britain and entitled "The Functionalization of Oligonucleotides Via Phosphoramidite Derivatives".

S. L. Beaucage, et al., Tetrahedron 48, 2223 to 2311 (1992) published in Great Britain and entitled "Advances in the Synthesis of Oligonucleotides by the Phosphoramidite Approach".

P. S. Nelson, et al., Nucleic Acids Research, 20, 6253 to 6259 (1992) published in Great Britain and entitled "Oligonucleotide labeling methods 3. Direct labeling of oligonucleotides employing a novel, non–nucleosidic, 2–aminobutyl–1,3–propanediol backbone".

S. L. Beaucage, et al., Tetrahedron 49, 6123 to 6194 (1993) published in Great Britain and entitled "The Synthesis of Modified Oligonucleotides by the Phosphoramidite Approach and Their Applications".

H. B. Gamper, et al., Nucleic Acids Research, 21, 145–150 (1993) published in Great Britain and entitled "Facile preparation of nuclease resistant 3' modified oligodeoxynucleotides".

M. J. Damha, et al., Nucleic Acids Research, 18, 3813 to 3821 (1990) published in Great Britain and entitled "An improved procedure for derivatization of controlled–pore glass beads for solid–phase oligonucleotide synthesis".

E. Sonveaux, Bioorganic Chemistry 14, 274 to 325 (1986) published in the United States and entitled "The Organic Chemistry Underlying DNA Synthesis".

S. Beck, et al., Analytical Chemistry, 62, 2258 to 2270 (1990) published in the United States and entitled "Perspective: Analytical Biotechnology Applications of Dioxetane Chemiluminescent Probes to Molecular Biology".

L. J. Ravin, Remington's Pharmaceutical Sciences, A. R. Gennaro, Editor, Mack Publishing Company, Easton, PA (1985), pp. 1409 to 1423 and entitled "Preformulation".

V. A. Efimov, et al., Nucleic Acids Research, 13, 3651 to 3666 (1985) published in England and entitled "Improved rapid phosphotriester synthesis of oligodeoxyribonucleotides using oxygen–nucleophilic catalysts".

B. Froehler, Tetrahedron Letters, 27, 5575 to 5578 (1986) published in Great Britain and entitled "Deoxynucleoside H–Phosphonate Diester Intermediates in the Synthesis of Internucleotide Phophate Analogues".

E. Uhlmann, et al., Chemical Reviews, 90, 544 to 584 (1990) published in the United States and entitled "Antisense Oligonucleotides: A New Therapeutic Principle".

C. Helene, et al., Biochemical et Biophysica Acta, 1049, 99 to 125 (1990) published in the Netherlands and entitled "Specific regulation of gene expression by antisense, sense and antigene nucleic acids".

V.N.T. Thuong, et al., Agnew. Chem. 105, 671 to 723 (1993) published in Germany and entitled "Sequence–specific recognition and modification of double helix DNA by oligonucleotides" and English translation thereof;.

D. Castanotto, et al., Critical Reviews in Eukaryotic Gene Expression 2, 331 to 357 (1992) published in the United States and entitled "Biological and Functional Aspects of Catalytic RNAs".

E. Uhlmann, et al., in Methods in Molecular Biology, vol. 20, Protocols for Oligonucleotides and Analogs, Edited by S. Agrawal, Humana Press Inc., Totowa, NJ and entitled "Oligonucleotide Analogs Containing Dephospho–Internucleoside Linkages", pp. 355 to 389 (1993).

SEQUENCE LISTING ( 1 ) GENERAL INFORMATION:

( i i i ) NUMBER OF SEQUENCES: 42

( 2 ) INFORMATION FOR SEQ ID NO:1:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: other nucleic acid ( x i ) SEQUENCE DESCRIPTION: SEQ ID NO:1:

ACACCCAATT CTGAAAATGG 20

( 2 ) INFORMATION FOR SEQ ID NO:2:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: other nucleic acid ( x i ) SEQUENCE DESCRIPTION: SEQ ID NO:2:

AGGTCCCTGT TCGGGCGCCA 20

( 2 ) INFORMATION FOR SEQ ID NO:3:

( i ) SEQUENCE CHARACTERISTICS:
        ( A ) LENGTH: 28 base pairs
        ( B ) TYPE: nucleic acid
        ( C ) STRANDEDNESS: single
        ( D ) TOPOLOGY: linear ( i i ) MOLECULE TYPE: other nucleic acid ( x i ) SEQUENCE DESCRIPTION: SEQ ID NO:3:

GTCGACACCC AATTCTGAAA ATGGATAA                                                                  28

( 2 ) INFORMATION FOR SEQ ID NO:4:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: other nucleic acid ( x i ) SEQUENCE DESCRIPTION: SEQ ID NO:4:

GCTATGTCGA CACCCAATTC TGAAA                                                                      25

( 2 ) INFORMATION FOR SEQ ID NO:5:

( i ) SEQUENCE CHARACTERISTICS:
        ( A ) LENGTH: 31 base pairs
        ( B ) TYPE: nucleic acid
        ( C ) STRANDEDNESS: single
        ( D ) TOPOLOGY: linear ( i i ) MOLECULE TYPE: other nucleic acid ( x i ) SEQUENCE DESCRIPTION: SEQ ID NO:5:

TCGTCGCTGT CTCCGCTTCT TCTTCCTGCC A                                                               31

( 2 ) INFORMATION FOR SEQ ID NO:6:

( i ) SEQUENCE CHARACTERISTICS:
        ( A ) LENGTH: 31 base pairs
        ( B ) TYPE: nucleic acid
        ( C ) STRANDEDNESS: single
        ( D ) TOPOLOGY: linear ( i i ) MOLECULE TYPE: other nucleic acid ( x i ) SEQUENCE DESCRIPTION: SEQ ID NO:6:

CTGTCTCCGC TTCTTCTTCT TGCCATAGGA G                                                               31

( 2 ) INFORMATION FOR SEQ ID NO:7:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: other nucleic acid ( x i ) SEQUENCE DESCRIPTION: SEQ ID NO:7:

GCGGGCTCC ATGGGGGTCG                                                                             20

( 2 ) INFORMATION FOR SEQ ID NO:8:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( i i ) MOLECULE TYPE: other nucleic acid ( x i ) SEQUENCE DESCRIPTION: SEQ ID NO:8:

CAGCTGCAAC CCAGC                                                                                 15

( 2 ) INFORMATION FOR SEQ ID NO:9:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: other nucleic acid ( x i ) SEQUENCE DESCRIPTION: SEQ ID NO:9:

GGCTGCTGGA GCGGGCACA C                                                      21

( 2 ) INFORMATION FOR SEQ ID NO:10:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( i i ) MOLECULE TYPE: other nucleic acid ( x i ) SEQUENCE DESCRIPTION: SEQ ID NO:10:

AACGTTGAGG GGCAT                                                           15

( 2 ) INFORMATION FOR SEQ ID NO:11:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: other nucleic acid ( x i ) SEQUENCE DESCRIPTION: SEQ ID NO:11:

GTGCCGGGGT CTTCGGGC                                                 18

( 2 ) INFORMATION FOR SEQ ID NO:12:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: other nucleic acid ( x i ) SEQUENCE DESCRIPTION: SEQ ID NO:12:

GGAGAACATC ATGGTCGAAA G                                        21

( 2 ) INFORMATION FOR SEQ ID NO:13:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: other nucleic acid ( x i ) SEQUENCE DESCRIPTION: SEQ ID NO:13:

CCCGAGAACA TCATGGTCGA AG                                      22

( 2 ) INFORMATION FOR SEQ ID NO:14:

( i ) SEQUENCE CHARACTERISTICS:
        ( A ) LENGTH: 20 base pairs
        ( B ) TYPE: nucleic acid (C) STRANDEDNESS: single
(D) TOPOLOGY: linear (ii) MOLECULE TYPE: other nucleic acid (xi) SEQUENCE DESCRIPTION: SEQ ID NO:14:

GGGGAAAGCC CGGCAAGGGG                    20

(2) INFORMATION FOR SEQ ID NO:15:

(i) SEQUENCE CHARACTERISTICS:
    (A) LENGTH: 20 base pairs
    (B) TYPE: nucleic acid
    (C) STRANDEDNESS: single
    (D) TOPOLOGY: linear (ii) MOLECULE TYPE: other nucleic acid (xi) SEQUENCE DESCRIPTION: SEQ ID NO:15:

CACCCGCCTT GGCCTCCCAC                    20

(2) INFORMATION FOR SEQ ID NO:16:

(i) SEQUENCE CHARACTERISTICS:
    (A) LENGTH: 18 base pairs
    (B) TYPE: nucleic acid
    (C) STRANDEDNESS: single
    (D) TOPOLOGY: linear (ii) MOLECULE TYPE: other nucleic acid (xi) SEQUENCE DESCRIPTION: SEQ ID NO:16:

GGGACTCCGG CGCAGCGC                      18

(2) INFORMATION FOR SEQ ID NO:17:

(i) SEQUENCE CHARACTERISTICS:
    (A) LENGTH: 20 base pairs
    (B) TYPE: nucleic acid
    (C) STRANDEDNESS: single
    (D) TOPOLOGY: linear (ii) MOLECULE TYPE: other nucleic acid (xi) SEQUENCE DESCRIPTION: SEQ ID NO:17:

GGCAAACTTT CTTTTCCTCC                    20

(2) INFORMATION FOR SEQ ID NO:18:

(i) SEQUENCE CHARACTERISTICS:
    (A) LENGTH: 19 base pairs
    (B) TYPE: nucleic acid
    (C) STRANDEDNESS: single
    (D) TOPOLOGY: linear (ii) MOLECULE TYPE: other nucleic acid (xi) SEQUENCE DESCRIPTION: SEQ ID NO:18:

GGGAAGGAGG AGGATGAGG                     19

(2) INFORMATION FOR SEQ ID NO:19:

(i) SEQUENCE CHARACTERISTICS:
    (A) LENGTH: 21 base pairs
    (B) TYPE: nucleic acid
    (C) STRANDEDNESS: single
    (D) TOPOLOGY: linear (ii) MOLECULE TYPE: other nucleic acid ( x i ) SEQUENCE DESCRIPTION: SEQ ID NO:19:

GGCAGTCATC CAGCTTCGGA G 21

( 2 ) INFORMATION FOR SEQ ID NO:20:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: other nucleic acid ( x i ) SEQUENCE DESCRIPTION: SEQ ID NO:20:

GCAGTAAGCA TCCATATC 18

( 2 ) INFORMATION FOR SEQ ID NO:21:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: other nucleic acid ( x i ) SEQUENCE DESCRIPTION: SEQ ID NO:21:

CCCCCACCAC TTCCCTCTC 20

( 2 ) INFORMATION FOR SEQ ID NO:22:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: other nucleic acid ( x i ) SEQUENCE DESCRIPTION: SEQ ID NO:22:

CTCCCCACC ACTTCCCTC 20

( 2 ) INFORMATION FOR SEQ ID NO:23:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: other nucleic acid ( x i ) SEQUENCE DESCRIPTION: SEQ ID NO:23:

GCTGGGAGCC ATAGCGAGG 19

( 2 ) INFORMATION FOR SEQ ID NO:24:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: other nucleic acid ( x i ) SEQUENCE DESCRIPTION: SEQ ID NO:24:

ACTGCTGCCT CTTGTCTCAG G 21

( 2 ) INFORMATION FOR SEQ ID NO:25:

( i ) SEQUENCE CHARACTERISTICS:
        ( A ) LENGTH: 9 base pairs
        ( B ) TYPE: nucleic acid
        ( C ) STRANDEDNESS: single
        ( D ) TOPOLOGY: linear ( i i ) MOLECULE TYPE: other nucleic acid ( x i ) SEQUENCE DESCRIPTION: SEQ ID NO:25:

TTTTTTTTN    9

( 2 ) INFORMATION FOR SEQ ID NO:26:

( i ) SEQUENCE CHARACTERISTICS:
        ( A ) LENGTH: 9 base pairs
        ( B ) TYPE: nucleic acid
        ( C ) STRANDEDNESS: single
        ( D ) TOPOLOGY: linear ( i i ) MOLECULE TYPE: other nucleic acid ( x i ) SEQUENCE DESCRIPTION: SEQ ID NO:26:

TTTTTTTTN    9

( 2 ) INFORMATION FOR SEQ ID NO:27:

( i ) SEQUENCE CHARACTERISTICS:
        ( A ) LENGTH: 8 base pairs
        ( B ) TYPE: nucleic acid
        ( C ) STRANDEDNESS: single
        ( D ) TOPOLOGY: linear ( i i ) MOLECULE TYPE: other nucleic acid ( x i ) SEQUENCE DESCRIPTION: SEQ ID NO:27:

TTTTTTTN    8

( 2 ) INFORMATION FOR SEQ ID NO:28:

( i ) SEQUENCE CHARACTERISTICS:
        ( A ) LENGTH: 8 base pairs
        ( B ) TYPE: nucleic acid
        ( C ) STRANDEDNESS: single
        ( D ) TOPOLOGY: linear ( i i ) MOLECULE TYPE: other nucleic acid ( x i ) SEQUENCE DESCRIPTION: SEQ ID NO:28:

TTTTTTTN    8

( 2 ) INFORMATION FOR SEQ ID NO:29:

( i ) SEQUENCE CHARACTERISTICS:
        ( A ) LENGTH: 8 base pairs
        ( B ) TYPE: nucleic acid
        ( C ) STRANDEDNESS: single
        ( D ) TOPOLOGY: linear ( i i ) MOLECULE TYPE: other nucleic acid ( x i ) SEQUENCE DESCRIPTION: SEQ ID NO:29:

TTTTTTTN    8

( 2 ) INFORMATION FOR SEQ ID NO:30:

( i ) SEQUENCE CHARACTERISTICS:
        ( A ) LENGTH: 8 base pairs
        ( B ) TYPE: nucleic acid -continued ( C ) STRANDEDNESS: single
                    ( D ) TOPOLOGY: linear ( i i ) MOLECULE TYPE: other nucleic acid ( x i ) SEQUENCE DESCRIPTION: SEQ ID NO:30:

TTTTTTTN                                                                                                    8

( 2 ) INFORMATION FOR SEQ ID NO:31:

( i ) SEQUENCE CHARACTERISTICS:
                    ( A ) LENGTH: 8 base pairs
                    ( B ) TYPE: nucleic acid
                    ( C ) STRANDEDNESS: single
                    ( D ) TOPOLOGY: linear ( i i ) MOLECULE TYPE: other nucleic acid ( x i ) SEQUENCE DESCRIPTION: SEQ ID NO:31:

TTTTTTTN                                                                                                    8

( 2 ) INFORMATION FOR SEQ ID NO:32:

( i ) SEQUENCE CHARACTERISTICS:
                    ( A ) LENGTH: 8 base pairs
                    ( B ) TYPE: nucleic acid
                    ( C ) STRANDEDNESS: single
                    ( D ) TOPOLOGY: linear ( i i ) MOLECULE TYPE: other nucleic acid ( x i ) SEQUENCE DESCRIPTION: SEQ ID NO:32:

TTTTTTTN                                                                                                    8

( 2 ) INFORMATION FOR SEQ ID NO:33:

( i ) SEQUENCE CHARACTERISTICS:
                    ( A ) LENGTH: 10 base pairs
                    ( B ) TYPE: nucleic acid
                    ( C ) STRANDEDNESS: single
                    ( D ) TOPOLOGY: linear ( i i ) MOLECULE TYPE: other nucleic acid ( x i ) SEQUENCE DESCRIPTION: SEQ ID NO:33:

GGACCGAAGN                                                                                                 10

( 2 ) INFORMATION FOR SEQ ID NO:34:

( i ) SEQUENCE CHARACTERISTICS:
                    ( A ) LENGTH: 8 base pairs
                    ( B ) TYPE: nucleic acid
                    ( C ) STRANDEDNESS: single
                    ( D ) TOPOLOGY: linear ( i i ) MOLECULE TYPE: other nucleic acid ( x i ) SEQUENCE DESCRIPTION: SEQ ID NO:34:

TTTTTTTN                                                                                                    8

( 2 ) INFORMATION FOR SEQ ID NO:35:

( i ) SEQUENCE CHARACTERISTICS:
                    ( A ) LENGTH: 8 base pairs
                    ( B ) TYPE: nucleic acid
                    ( C ) STRANDEDNESS: single
                    ( D ) TOPOLOGY: linear ( i i ) MOLECULE TYPE: other nucleic acid ( x i ) SEQUENCE DESCRIPTION: SEQ ID NO:35:

TTTTTTN  8

( 2 ) INFORMATION FOR SEQ ID NO:36:

( i ) SEQUENCE CHARACTERISTICS:
        ( A ) LENGTH: 8 base pairs
        ( B ) TYPE: nucleic acid
        ( C ) STRANDEDNESS: single
        ( D ) TOPOLOGY: linear ( i i ) MOLECULE TYPE: other nucleic acid ( x i ) SEQUENCE DESCRIPTION: SEQ ID NO:36:

TTTTTTN  8

( 2 ) INFORMATION FOR SEQ ID NO:37:

( i ) SEQUENCE CHARACTERISTICS:
        ( A ) LENGTH: 8 base pairs
        ( B ) TYPE: nucleic acid
        ( C ) STRANDEDNESS: single
        ( D ) TOPOLOGY: linear ( i i ) MOLECULE TYPE: other nucleic acid ( x i ) SEQUENCE DESCRIPTION: SEQ ID NO:37:

TTTTTTN  8

( 2 ) INFORMATION FOR SEQ ID NO:38:

( i ) SEQUENCE CHARACTERISTICS:
        ( A ) LENGTH: 8 base pairs
        ( B ) TYPE: nucleic acid
        ( C ) STRANDEDNESS: single
        ( D ) TOPOLOGY: linear ( i i ) MOLECULE TYPE: other nucleic acid ( x i ) SEQUENCE DESCRIPTION: SEQ ID NO:38:

TTTTTTN  8

( 2 ) INFORMATION FOR SEQ ID NO:39:

( i ) SEQUENCE CHARACTERISTICS:
        ( A ) LENGTH: 8 base pairs
        ( B ) TYPE: nucleic acid
        ( C ) STRANDEDNESS: single
        ( D ) TOPOLOGY: linear ( i i ) MOLECULE TYPE: other nucleic acid ( x i ) SEQUENCE DESCRIPTION: SEQ ID NO:39:

TTTTTTN  8

( 2 ) INFORMATION FOR SEQ ID NO:40:

( i ) SEQUENCE CHARACTERISTICS:
        ( A ) LENGTH: 8 base pairs
        ( B ) TYPE: nucleic acid
        ( C ) STRANDEDNESS: single
        ( D ) TOPOLOGY: linear ( i i ) MOLECULE TYPE: other nucleic acid ( x i ) SEQUENCE DESCRIPTION: SEQ ID NO:40:

TTTTTTN  8

(2) INFORMATION FOR SEQ ID NO:41:

(i) SEQUENCE CHARACTERISTICS:
(A) LENGTH: 15 base pairs
(B) TYPE: nucleic acid
(C) STRANDEDNESS: single
(D) TOPOLOGY: linear (ii) MOLECULE TYPE: other nucleic acid (xi) SEQUENCE DESCRIPTION: SEQ ID NO:41:

CACGTTGAGG GGCAN    15

(2) INFORMATION FOR SEQ ID NO:42:

(i) SEQUENCE CHARACTERISTICS:
(A) LENGTH: 15 base pairs
(B) TYPE: nucleic acid
(C) STRANDEDNESS: single
(D) TOPOLOGY: linear (ii) MOLECULE TYPE: other nucleic acid (xi) SEQUENCE DESCRIPTION: SEQ ID NO:42:

CACGTTGAGG GGCAN    15

3'-MODIFIED OLIGONUCLEOTIDE DERIVATIVES

The present invention relates to novel oligonucleotide analogs with valuable physical, biological and pharmacological properties and to a process for the preparation thereof. Application thereof relates to the use as inhibitors of gene expression (antisense oligonucleotides, ribozymes, sense oligonucleotides and triplex forming oligonucleotides), as probes for detecting nucleic acids and as aids in molecular biology.

Oligonucleotides are increasingly being used as inhibitors of gene expression (J. F. Milligan, M. D. Matteucci and J. C. Martin, J. Med. Chem. 36 (1993) 1923; E. Uhlmann and A. Peyman, Chemical Reviews 90 (1990) 543).

Antisense oligonucleotides are nucleic acid fragments whose base sequence is complementary to a mRNA to be inhibited. This target mRNA may be of cellular, viral or other pathogenic origin. Examples of appropriate cellular target sequences are those of receptors, enzymes, growth factors, immunomodulators, ion channels or oncogenes. Inhibition of virus replication using antisense oligonucleotides has been described, for example, for RSV (Rous sarcoma virus), HSV-1 and -2 (herpes simplex virus type I and II), HIV (human immunodeficiency virus) and influenza viruses. This entails use of oligonucleotides which are complementary to the viral nucleic acid.

Sense oligonucleotides are, by contrast, designed in their sequence so that they bind ("trap"), for example, nucleic acid-binding proteins or nucleic acid-processing enzymes and thus inhibit the biological activity thereof (C. Hélène and J. J. Toulmé, Biochim. Biophys. Acta 1049 (1990) 99). Examples of viral targets which may be mentioned in this connection are reverse transcriptase, DNA polymerase and transactivator proteins. Triplex forming oligonucleotides generally have DNA as target and, after binding thereto, form a triple helix structure.

Whereas antisense oligonucleotides are used in general to inhibit the processing (splicing etc.) of the mRNA or the translation thereof into protein, triplex forming oligonucleotides inhibit the transcription or replication of DNA (N. T. Thuong and C. Hélèe, Angew. Chem. 105 (1993) 697; Uhlmann and Pepan, Chemical Reviews 90 (1990) 543). However, it is also possible to bind single-stranded nucleic acids in a first hybridization with an antisense oligonucleotide to form a double strand which then, in a second hybridization with a triplex-forming oligonucleotide, forms a triplex structure. The antisense and triplex binding regions can moreover be located either in two separate oligonucleotides or else in one oligonucleotide.

A further application of synthetic oligonucleotides is in so-called ribozymes which destroy the target RNA as a consequence of their ribonuclease activity (D. Castanotto, J. J. Rossi, J. O. Deshler, Critical Rev. Eukar. Gene Expr. 2 (1992) 331).

Nucleic acid fragments with suitable labeling are used in DNA diagnosis as so-called DNA probes for specific hybridization onto a nucleic acid which is to be detected. The specific formation of the new double strand is in this case followed by means of the labeling, which is preferably not radioactive. It is possible in this way to detect genetic, malignant or vital diseases or diseases caused by other pathogene.

For most of the said applications, oligonucleotides in their naturally occurring form are of little suitability or completely unsuitable. They must be chemically modified so that they meet specific requirements. For oligonucleotides to be usable in biological systems, for example inhibiting virus replication, they must comply with the following conditions:

1. They must have a sufficiently high stability under in vivo conditions, that is to say both in serum and inside cells.
2. Their properties must be such that they can pass through the plasma membrane and nuclear membrane.
3. They must under physiological conditions bind in a base-specific manner to their target nucleic acid in order to display the inhibitory effect.

These conditions are not indispensable for DNA probes; however, these oligonucleotides must be derivatized in such a way that detection, for example, by fluorescence, chemiluminescence, colorimetry or specific staining, is possible (Beck and Köster, Anal. Chem. 62 (1990) 2258).

Chemical modification of oligonucleotides usually takes place by appropriate modification of the phosphate backbone, ribose unit or the nucleotide bases (Uhlmann and Peyman, Chemical Reviews 90 (1990) 543). Another frequently used method is to prepare oligonucleotide 5'-conjugates by reacting the 5'-hydroxyl group with appropriate phosphorylation reagents. Oligonucleotides modified only at the 5' end have the disadvantage that they are broken down in serum. If, on the other hand, all the internucleotide phosphate residues are modified there are often drastic alterations in the properties of the oligonucleotides. For example, the solubility of methylphosphonate oligonucleotides in aqueous medium is diminished and the hybridization capacity is reduced. Phosphorothioate oligonucleotides have non-specific effects so that, for example, even homooligomers (Uhlmann and Pepan, Chemical Reviews 90 (1990) 543) are active against viruses.

The breakdown of oligonucleotides by 3'-nucleolytic activity is generally regarded as the predominant breakdown by nucleases in serum. The object therefore is to provide 3'-derivatized oligonucleotide analogs with specific activity, increased serum stability and good solubility.

This invention therefore relates to compounds of the formula I and formula II

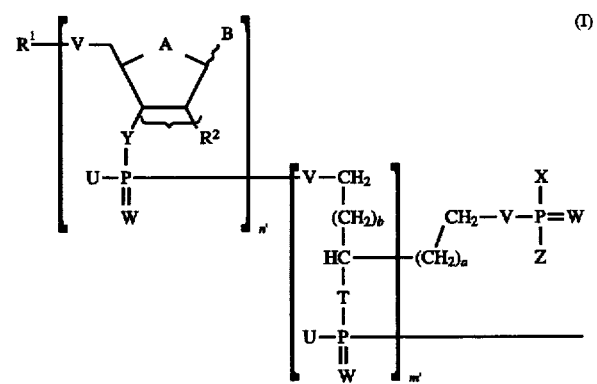

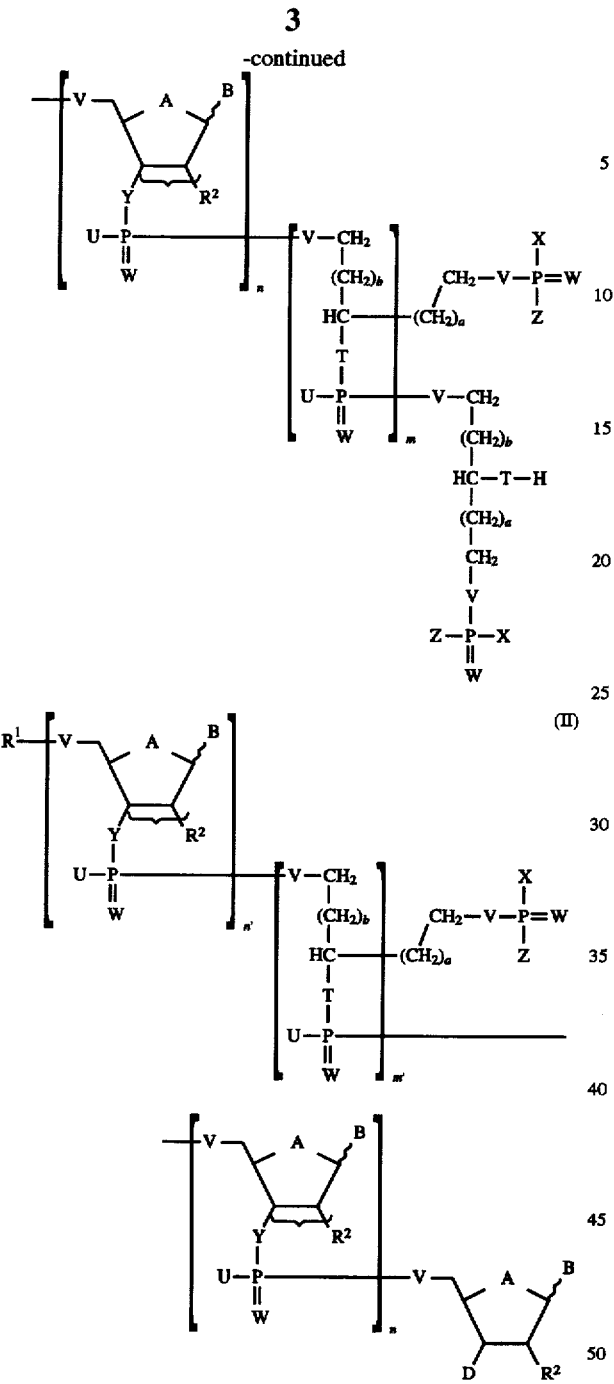

and the physiologically tolerated salts thereof, in which a is a number from zero to 20, preferably from zero to 10, particularly preferably from zero to 6, very particularly preferably from zero to 4;

b is a number from zero to 20, preferably from zero to 10, particularly preferably from zero to 4, very particularly preferably of zero;

$R^1$ is hydrogen, $C_1$–$C_{18}$-alkyl, preferably $C_1$–$C_6$-alkyl, in particular methyl, $C_2$–$C_{18}$-alkenyl, $C_3$–$C_{18}$-alkynyl, $C_1$–$C_{18}$-alkylcarbonyl, $C_2$–$C_{19}$-alkenylcarbonyl, $C_3$–$C_{19}$-alkynylcarbonyl, $C_6$–$C_{20}$-aryl, $C_6$–$C_{14}$-aryl-$C_1$–$C_8$-alkyl, or a radical of the formula III

preferably hydrogen or a radical of the formula III, very particularly preferably hydrogen;

$R^2$ is hydrogen, hydroxyl, $C_1$–$C_{18}$-alkoxy, halogen, azido or $NH_2$, preferably hydrogen, hydroxyl, $C_1$–$C_4$-alkoxy, fluorine or $NH_2$, particularly preferably hydrogen or hydroxyl, very particularly preferably hydrogen;

D is hydroxyl, O—$PO_2^{2-}$, very particularly preferably hydroxyl;

B is a base customary in nucleotide chemistry, for example natural bases such as adenine, cytosine, guanine, uracil and thymine or unnatural bases such as, for example, purine, 2,6-diaminopurine, 7-deazaadenine, 7-deazaguanine, $N^4,N^4$-ethanocytosine, $N^6,N^6$-ethano-2,6-diaminopurine, pseudoisocytosine, 5-propinuracil, 5-propincytosine, 5-fluorocytosine, 5-fluorouracil, 5-hydroxymethyluracil and 5-bromoaytosine and very particularly preferably adenine, cytosine, guanine, uracil, thymine, 5-propinuracil and 5-propincytosine;

n is an integer from 1 to 100, preferably 5 to 40, particularly preferably 6 to 30, very particularly preferably 7 to 25;

n' is an integer from zero to 50, preferably zero to 40, particularly preferably zero to 30, very particularly preferably zero to 25;

m is an integer from zero to 5, very particularly preferably zero;

m' in formula I is an integer from zero to 5, very particularly preferably zero or 1;

m' in formula II is an integer from 1 to 5, very particularly preferably 1;

A is oxy, thioxy or methylene, preferably oxy;

W is oxo, thioxo or selenoxo, preferably oxo or thioxo, particularly preferably oxo;

V is oxy or thio, very particularly preferably oxy,

T is oxy, thio or imino, very particularly preferably oxy;

Y is oxy, thio, imino or methylene, very particularly preferably oxy;

X is hydroxyl or mercapto;

U is hydroxyl, mercapto, $BH_3$, SeH, $C_1$–$C_{18}$-alkoxy, preferably $C_1$–$C_6$-alkoxy, $C_1$–$C_{18}$-alkyl, preferably $C_1$–$C_6$-alkyl, $C_6$–$C_{20}$-aryl, $C_6$–$C_{14}$-aryl-$C_1$–$C_{18}$-alkyl, $NHR^3$, $NR^3R^4$ or a radical of the formula IV $$(OCH_2CH_2)_pO(CH_2)_qCH_2R^5 \quad (IV)$$

preferably hydroxyl, mercapto, $C_1$–$C_6$-alkoxy, $C_1$–$C_6$-alkyl, $NR^3R^4$ or $NHR^3$ and particularly preferably hydroxyl or $C_1$–$C_6$-alkyl, in which $R^3$ is $C_1$–$C_{18}$-alkyl, preferably $C_1$–$C_{18}$-alkyl, $C_6$–$C_{20}$-aryl, $C_6$–$C_{14}$-aryl-$C_1$–$C_8$-alkyl, —$(CH_2)_c$—[NH1 $(CH_2)_c]_d$—$NR^6R^6$, in which c is an integer from 2 to 6 and d is an integer from zero to 6, and $R^6$ is, independently of one another, hydrogen, $C_1$–$C_6$-alkyl or $C_1$–$C_4$-alkoxy-$C_1$–$C_6$-alkyl, preferably methoxyethyl, preferably $C_1$–$C_8$-alkyl, in particular $C_1$–$C_4$-alkyl;

$R^4$ is $C_1$–$C_{18}$-alkyl, $C_6$–$C_{20}$-aryl or $C_6$–$C_{10}$-aryl-$C_1$–$C_8$-alkyl, preferably $C_1$–$C_8$-alkyl, in particular $C_1$–$C_4$-alkyl, $C_6$–$C_{20}$-aryl or $C_6$–$C_{10}$-aryl-$C_1$–$C_8$-alkyl, or, in the case of $NR^3R^4$, is, together with $R^3$ and the nitrogen atom carrying them, a 5–6-membered heterocyclic ring which can additionally contain another hetero atom from the series consisting of O, S and N;

p is an integer from 1 to 100, preferably 3 to 20 and particularly preferably 3 to 8;

q is an integer from zero to 22, preferably zero to 15;

$R^5$ is hydrogen or a functional group such as hydroxyl, amino, $NHR^7$, COOH, $CONH_2$, $COOR^8$ or halogen, in which $R^7$ is $C_1-C_6$-alkyl and $R^8$ is $C_1-C_4$-alkyl, preferably methyl;

Z and Z' are, independently of one another, hydroxyl, mercapto, SeH, $C_1-C_{22}$-alkoxy, preferably $C_6-C_{18}$-alkoxy, —O-$(CH_2)_b$—$NR^7R^8$, in which b is an integer from 1 to 6, and $R^7$ is $C_1-C_6$-alkyl and $R^8$ is $C_1-C_4$-alkyl, or $R^7$ and $R^8$ form, together with the nitrogen atom carrying them, a 3–6-membered ring; $C_1-C_{18}$-alkyl, preferably $C_1-C_8$-alkyl, $C_6-C_{20}$-aryl, $C_6-C_{14}$-aryl-$C_1-C_8$-alkyl, preferably $C_6-C_{10}$-aryl-$C_1-C_4$-alkyl, $C_6-C_{14}$-aryl-$C_1-C_8$-alkoxy, preferably $C_6-C_{10}$-aryl-$C_1-C_4$-alkoxy, where aryl also means heteroaryl and aryl is optionally substituted by 1, 2 or 3 identical or different radicals from the series consisting of carboxyl, amino, nitro, $C_1-C_4$-alkylamino, $C_1-C_6$-alkoxy, hydroxyl, halogen and cyano, or $C_1-C_{18}$-alkylmercapto, $NHR^3$, $NR^3R^4$, in which $R^3$ and $R^4$ are as defined above, or a group which favors intracellular uptake or acts as labeling of a DNA probe or, on hybridization of the oligonucleotide analog onto to the target nucleic acid, interacts with the latter by binding, crosslinking or cleavage, or a nucleoside or oligonucleotide linked via the 5' or 3' ends; and the curved parenthesis indicates that $R^2$ and the adjacent phosphoryl radical can be located in the 2' and 3' positions or else conversely in the 3' and 2' positions, it being possible for each nucleotide to be in its D or L configuration and for the base B to be located in the α or β position.

Oligonucleotide analogs of the formula I and the physiologically tolerated salts thereof in which the base B is located in the β position, the nucleotides are in the D configuration and $R^2$ is located in the 2' position are preferred.

Oligonucleotide analogs of the formula I in which V and Y are oxy are particularly preferred.

Also particularly preferred are oligonucleotide analogs of the formula I in which V, Y and W are oxy and oxo respectively.

Oligonucleotide analogs of the formula I in which V, Y, W and Y are oxy, oxo and hydroxyl, respectively, are very particularly preferred.

Oligonucleotide analogs of the formula I in which $R^1$ is hydrogen are furthermore preferred.

Oligonucleotide analogs of the formula I in which U, V, W, X and Y are oxy, oxo and hydroxyl, respectively, and $R^1$ is hydrogen, are particularly preferred.

The radicals which occur repeatedly, such as $R^2$, B, A, W, V, Y, U, $R^3$, $R^4$, T, a, b, p, q and Z can have meanings which are identical or different independently of one another, i.e., for example, V is, independently of one another, oxy, thio or imino.

Halogen is preferably fluorine, chlorine or bromine.

Heteroaryl means, in particular, radicals derived from phenyl or naphthyl in which one or more CH groups are replaced by N and/or in which at least two adjacent CH groups are replaced by S, NH or O (to form a five-membered aromatic ring). Furthermore, one or both atoms at the point of fusion in bicyclic radicals (as indolizinyl) can be nitrogen atoms. Heteroaryl is, in particular, furanyl, thienyl, pyrrolyl, imidazolyl, pyrazolyl, triazolyl, tetrazolyl, oxazolyl, isoxazolyl, thiazolyl, isothiazolyl, pyridyl, pyrazinyl, pyrimidinyl, pyridazinyl, indolyl, indazolyl, quinolyl, isoquinolyl, phthalazinyl, quinoxalinyl, quinazolinyl, cinnolinyl.

Examples of groups which favor intracellular uptake are various lipophilic radicals such as —O-$(CH_2)_x$—$CH_3$ in which x is an integer from 6–18, —O-$(CH_2)_e$—CH=CH—()$CH_2)_f$—$CH_3$ in which e and f are, independently of one another, an integer from 6 to 12, —O-$(CH_2CH_2O)_4$—$(CH_2)_9$—$CH_3$, —O-$(CH_2CH_2O)_8$—$(CH_2)_{13}$—$CH_3$ and —O-$(CH_2CH_2O)_7$—$(CH_2)_{15}$—$CH_3$, but also steroid residues such as cholesteryl and conjugates which utilize natural carrier systems, such as bile acid, folic acid, 2-(N-alkyl-N-alkoxy)aminoanthraquinone and conjugates of mannose and peptides of the appropriate receptors which lead to receptor-mediated endocytosis of the oligonucleotides, such as EGF (epidermal growth factor), bradykinin and PDGF (platelet derived growth factor). Labeling groups mean fluorescent groups, for example of dansyl (=N-dimethyl-1-aminonaphthyl-5-sulfonyl), fluorescein or coumarin derivatives or chemiluminescent groups, for example of acridine derivatives, and the digoxigenin system detectable by ELISA, the biotin group detectable via the biotin/avidin system, or else linker arms with functional groups which permit subsequent derivatization with detectable reporter groups, for example an aminoalkyl linker, which is reacted with an acridinium active ester to give the chemiluminescent sample. Typical labeling groups are:

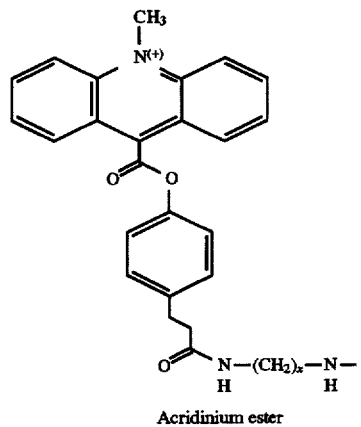

Acridinium ester

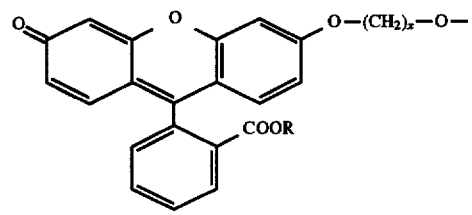

Fluorescein derivative    x = 2–18, preferably 4
R = H or $C_1-C_4$-alkyl
(= "fluorescein" for
x = 4 and R = $CH_3$)

R = H or amino protective group

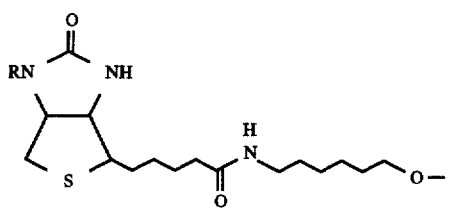

Biotin conjugate (= "biotin" for R = Fmoc)

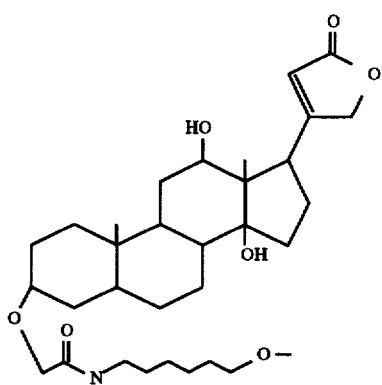

Digoxigenin conjugate

Oligonucleotide analogs which bind or intercalate and/or cleave or crosslink to nucleic acids contain, for example, acridine, psoralen, phenanthroline, naphthoquinone, daunomycin or chloroethylaminoaryl conjugates. Typical intercalating and crosslinking radicals are:

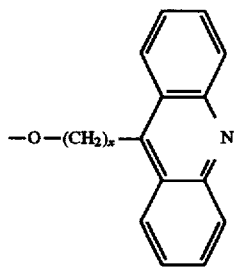

Acridine derivative x = 2–12, preferably 4

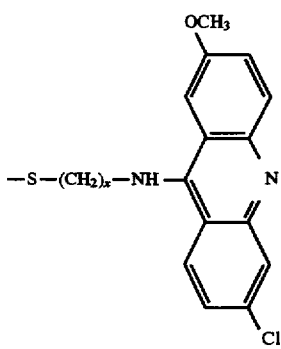

x = 2–12, preferably 4

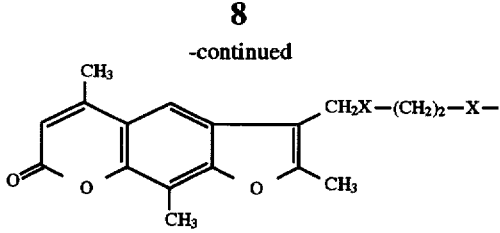

X = —NH or —O—
Trimethylpsoralen conjugate (= "psoralen" for X=O)

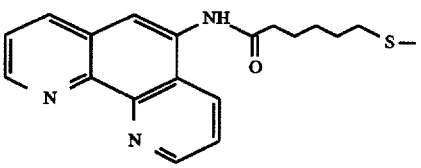

Phenanthroline conjugate

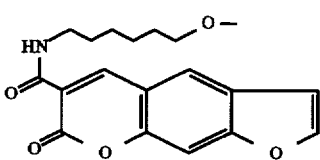

Psoralen conjugate

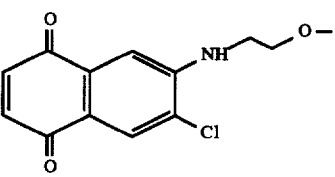

Naphthoquinone conjugate

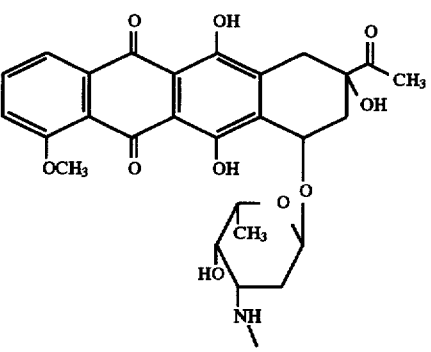

Daunomycin derivative

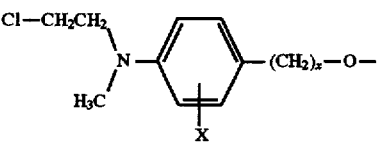

x = 1–18, X = alkyl, halogen, NO$_2$, CN, —C(=O)—R

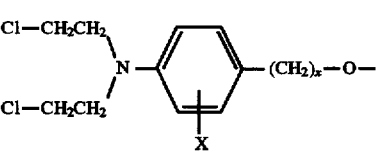

x = 1–18, X = alkyl, halogen, NO$_2$, CN, —C(=O)—R

The invention is not confined to α- and β-D- or L-ribofuranosides, α- and β-D- or L-deoxyribofuranosides and corresponding carbocyclic five-membered ring analogs but also applies to oligonucleotide analogs which are assembled from different sugar building blocks, for example ring-expanded and ring-contracted sugars, acyclic or suitable other types of sugar derivatives. The invention is furthermore not confined to the derivatives, listed by way of example in formula I and formula II, of the phosphate residue but also relates to the known dephospho derivatives (E. Uhlmann and A. Peyman in "Methods in Molecular Biology", Vol. 20, Protocols for Oligonucleotides and Analogs. S. Agarwal, Ed., Humana Press, Ottowa 1993). The invention also relates to other modifications familiar in the chemistry of oligonucleotide analogs, for example known conjugate modifications via phosphate residues, bases and at the 3' end in the case of formula II. The invention furthermore also relates to oligonucleotides in which the novel building blocks can additionally be present elsewhere in compounds of the formulae I and II.

Physiologically tolerated salts of compounds of the formulae I and II mean both inorganic and organic salts as described in Remington's Pharmaceutical Sciences (Mack Publ. Co., Easton, Pa., 17th edition (1985) 1418). Because of the physical and chemical stability, inter alia sodium, potassium, calcium and ammonium salts are preferred for acidic groups.

Oligonucleotide analogs of the formula I and II are prepared by known methods analogous to the synthesis of biological oligonucleotides in solution or, preferably, on solid phase, where appropriate with the assistance of an automatic synthesizer.

There are various methods for introducing conjugate molecules at the 3' end of the oligonucleotides. However, these do not afford compounds of the formula I. A review of the prior art is given by: M. Manoharan in Antisense Research and Applications, Crooke and Lebleu, Eds., Chapter 17, pages 303 et seq., CRC Press Boca Raton, 1993, and EP-A 0 552 766 (HOE 92/F 012) and EP-A 0 552 767 (HOE 92/F 013). Whereas derivatization at the 5' end of an oligonucleotide is comparatively simple to bring about, for example by reaction with a phosphoramidite of the appropriate conjugate molecule using the standard oligonucleotide synthesis cycle, there is no such universally applicable process for the 3' end. 3'-conjugation takes place either post-synthetically—that is to say after elimination from the support and after elimination of the protective groups—or via a support material which is to be prepared specifically for a specific conjugate molecule. P. S. Nelson et al. (Nucl. Acids Res. 20 (1992) 6253) describe a 3' linker from which, after synthesis has taken place on the solid support, all protective groups are eliminated and then conjugate molecules are coupled onto the free amino group post-synthetically. Gamper et al. (Nucl. Acids Res. 21 (1993) 145) describe solid-phase synthesis using support material which has been derivatized with the conjugate molecule to be introduced. The support must be derivatized in an elaborate manner for every conjugate molecule. EP-A 0 552 766 and EP-A 0 552 767 describe a β-eliminatable linker onto which are coupled nucleoside phosphoramidites which carry the appropriate conjugate molecule in place of the usual cyanoethyl protective group. The oligonucleotide synthesis then takes place. This means that the conjugate molecule must not carry any acid-labile protective group, which would be eliminated during the synthesis cycle. In addition, the synthesis of the nucleoside conjugate monomer building blocks is very elaborate.

This invention therefore relates to a process which can be employed universally for the 3' modification of oligonucleotides on a solid support, which permits the introduction of a conjugate molecule by phosphoramidite chemistry during solid-phase synthesis. It is possible to employ for the conjugation the readily accessible conjugate phosphoramidites which are familiar for 5' derivatization. The linker molecule with the appropriate protective group which is used for this purpose can be introduced not only at the 3' end of the oligonucleotide but also one or more times within the oligonucleotide using phosphoramidite chemistry.

The process for the preparation of the compounds of the formula I comprises a) reacting a compound of the formula V

in which a, b, V, T are defined as above in formula I and

V' is V, and the functional groups V, V' and T can also be in temporarily protected form where appropriate (preferably, if V=V'=T=oxy and b=0, as cyclic acetal which is obtained by reaction with acetone with Fe$^{III}$ catalysis and is eliminated again with acetic acid after introduction of the protective group S1), with a protective group S1 which can be eliminated from an oligonucleotide which is still completely protected and linked to the support without cleaving other protective groups or the linkage to the solid support, such as, for example, the levuloyl protective group, and ortho-, meta- or para-R-O-aryl, where R is $C_1$–$C_{20}$-alkyl, $C_2$–$C_{20}$-alkenyl, $C_3$–$C_{20}$-alkynyl, $C_6$–$C_{12}$-aryl-$C_1$–$C_6$-alkyl, preferably the levuloyl protective group and the para-methoxyphenyl protective group, and a protective group S2 which can be removed without cleaving the linker arm Li in formula VII and without cleaving the protective group S1, preferably dimethoxytrityl, monomethoxytrityl, trityl, pixyl, 4-methoxytetrahydropyranyl, particularly preferably monomethoxytrityl and dimethoxytrityl, by known processes (for example M. J. Gait, "Oligonucleotide Synthesis—a practical approach", IRL Press 1984), for example the para-methoxyphenyl group is introduced by reaction with para-methoxyphenol, diphenyl azodicarboxylate and triphenylphosphine in a suitable solvent, for example tetrahydrofuran (THF), under reflux, then the acetal is eliminated again with acid, for example with acetic acid, and subsequently the monomethoxytrityl protective group is introduced by reaction with monomethoxytrityl chloride in pyridine, to give a compound of the formula VI

in which

S1, S2, V, V', T, a and b are as defined above, b) subsequently reacting the compound of the formula VI by known processes with 1 to 10 equivalents, preferably with 1 to 2 equivalents, of a linker Li such as, for example, succinic anhydride, in a suitable organic solvent such as, for example, methylene chloride, where appropriate after addition of a catalyst, for example 4-dimethylaminopyridine, to give a compound of the formula VII

in which

S1, S2, V, V', T, a and b are as defined above, and

Li is a linker arm which can attach the compound of the formula VI by chemical linkage (emide, ester, inter alia) to a solid support (Damka et al., Nucleic Acids Res. 18 (1990) 3813, Sonveaux (Bioorg. Chem. 14 (1986) 274), preferably a succinic acid residue (O—C(O)—C(O)—), an alkylamine, preferably LCAA (long chain alkylemine), or polyethylene glycol, particularly preferably a succinic acid residue, where in certain cases, for example in combination with substituents which do not withstand lengthy ammonia treatment, also more labile linkers such as the oxalyl linker are advantageous, and subsequently working up by known processes, such as, for example, extraction, crystallization, chromatography;

c) coupling the compound of the formula VII by known processes to a solid support SS such as, for example, aminopropyl-CPG (CPG=controlled pore glass) or ®Tentagel (from Rapp, Germany), for example by reaction with DCC and p-nitrophenol in a suitable solvent with O-(benzotriazol-1-yl)-N,N,N',N'-tetramethyluronium tetrafluoroborate (TBTU) and a base such as, for example, N-ethylmorpholine, in a suitable solvent such as, for example, DMF (for example M. J. Gait, Oligonucleotide Synthesis—a practical approach, IRL Press, 1984) to obtain a compound of the formula VIII

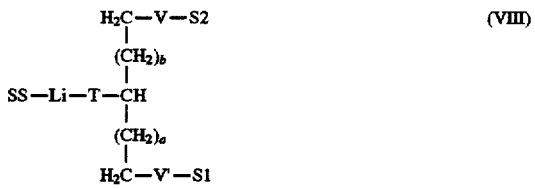

in which

S1, S2, V, V', T, Li, a and b are as defined above, and SS is the solid support, for example of materials such as CPG (controlled pore glass), silica gel or an organic resin such as polystyrene (PS) or a graft copolymer of PS and polyethylene glycol (POE), and is modified by functional groups such as hydroxyl, amino, halogen or COOH in the side chain:

d) eliminating the protective group S2 by known processes, for example by treatment with 1–4% dichloroacetic acid (DCA) in dichloromethane or chloroform, or alternatively previously eliminating the protective group S1 by known processes, for example the levuloyl protective group by treatment with hydrazine, carrying out reaction steps l) and m), then reaction steps e)–i) and subsequently reaction step n), or alternatively after elimination of the protective group S2 carrying out reaction steps l) and m), then eliminating the protective group S1 by known processes, for example the levuloyl protective group by treatment with hydrazine or the para-methoxyphenyl protective group by treatment with $Ce^{IV}$, then parrying out reaction steps e)–i) and finally reaction step n);

e) subsequently, if m is 1 to 5, reacting the compound obtained in d) with a compound of the formula IX

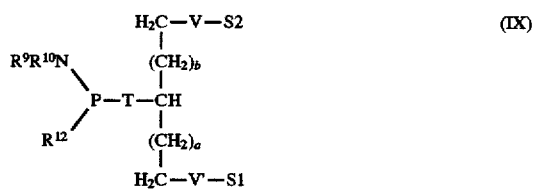

in which

S1, S2, V, V', T, a and b are as defined above, and $R^9$ and $R^{10}$ are identical or different and are $C_{1-8}$-alkyl, preferably isopropyl, or $C_5$–$C_{12}$-cycloalkyl, preferably up to $C_8$, benzyl or phenyl or together with the nitrogen atom to which they are bonded a saturated or unsaturated heterocyclic ring, optionally with further hetero atoms, such as, for example, morpholine, and substituents such as $OC(O)O$—$C_1$–$C_4$-alkyl esters, $R^{12}$ is $OR^{13}$ or $C_1$–$C_{18}$-alkyl, $C_1$–$C_{18}$-alkoxy, $C_6$–$C_{20}$-aryl, $C_6$–$C_{14}$-aryl-$C_1$–$C_8$-alkyl, preferably $OR^{13}$, $C_1$–$C_6$-alkyl, $C_1$–$C_6$-alkoxy, $C_6$–$C_{20}$-aryl, $C_6$–$C_{14}$-aryl-$C_1$–$C_8$-alkyl, particularly preferably $OR^{13}$ or $C_1$–$C_6$-alkyl, $R^{13}$ is a group of the formulae

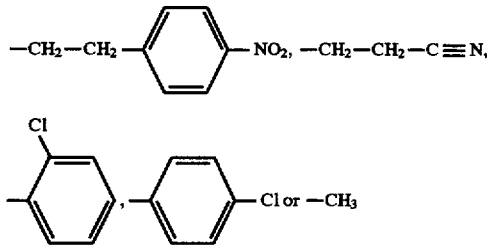

or a benzyl group, which is not or is one to four times ring-substituted, preferably not substituted, where the substituent or substituents is, independently of one another, fluorine, chlorine, bromine, a $C_1$–$C_4$-alkyl, nitro, methoxy or carboxyl group, in the presence of a compound of the formula $[HNR^{14}R^{15}R^{16}]^{(+)}E^{(-)}$, where $R^{14}$, $R^{15}$ and $R^{16}$ are identical to or different from one another and are a $C_1$–$C_4$-alkyl group and E is fluorine, chlorine, bromine, in particular chlorine, or in the presence of tetrazole or substituted tetrazole, such as, for example, 5-(4-nitrophenyl)-1H-tetrazole or 5-methylthio-1H-tetrazole or 5-ethylthio-1H-tetrazole, preferably in the presence of substituted tetrazole such as, for example, 5-(4-nitrophenyl)-1H-tetrazole or 5-methylthio-1H-tetrazole or 5-ethylthio-1H-tetrazole, particularly preferably in the presence of 5-methylthio-1H-tetrazole, in a suitable organic solvent, preferably acetonitrile, oxidizing the resulting compound by known processes, for example as described in reaction step m), carrying out a capping in the conventional way, eliminating the protective group S2 (for example Beaucage and Iyer Tetrahedron 49 (1993) 1925 & 2223 & 6123; E. Sonveaux, Bioorg. Chem. 14 (1986) 274; E. Uhlmann and A. Peyman, Chemical Reviews 90 (1990) 543) and, then repeating this reaction step (m-1) times where appropriate, resulting in a compound of the formula X

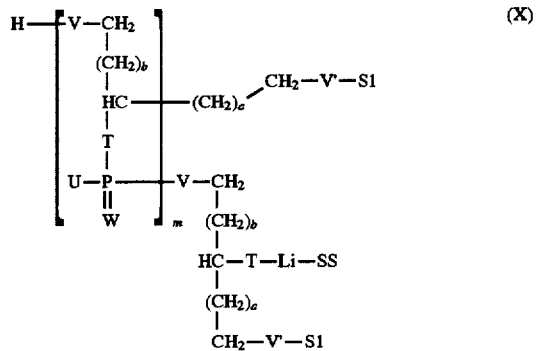

in which Li, S1, SS, T, U, V, V', W, a, b and m are as defined above;

f) if m is 0, reacting the compound obtained in d) by the phosphoramidite method (E. Sonveaux, Bioorg. Chem. 14 (1986) 274) with a nucleoside phosphoramidite of the formula XI

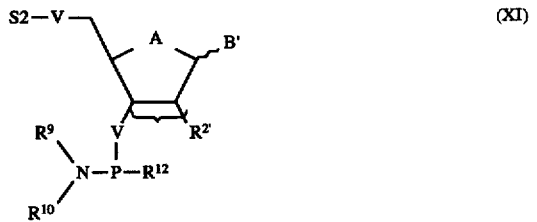

in which

B' is defined as B and $R^{2'}$ is defined as $R^2$, and these can also be in protected form where appropriate, for example $R^2$ can be hydroxyl protected by tert-butyldimethylsilyl, and $R^9$, $R^{10}$, $R^{12}$, S2 and V are as defined above, oxidizing the resulting compound by known processes, carrying out a capping in the conventional way, eliminating the protective group S2, preferably dimethoxytrityl or monomethoxytrityl, by known processes (for example Beaucage and Iyer, Tetrahedron 49 (1993) & 2223 & 6123; E. Sonveaux, Bioorg. Chem. 14 (1986) E. Uhlmann and A. Peyman, Chemical Reviews 90 (1990) and then repeating this reaction step (n-1) times where appropriate, resulting in a compound of the formula XII

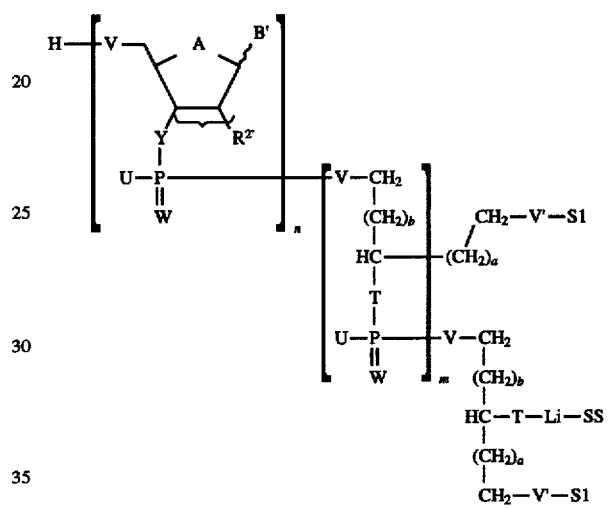

in which A, B', Li, $R^{2'}$, S1, SS, T, U, V, V', W, Y, a, b, m and n are as defined above;

g) if m' is 1 to 5, carrying out reaction step e), which is repeated (m-1) times where appropriate, resulting in the compound of the formula XIII

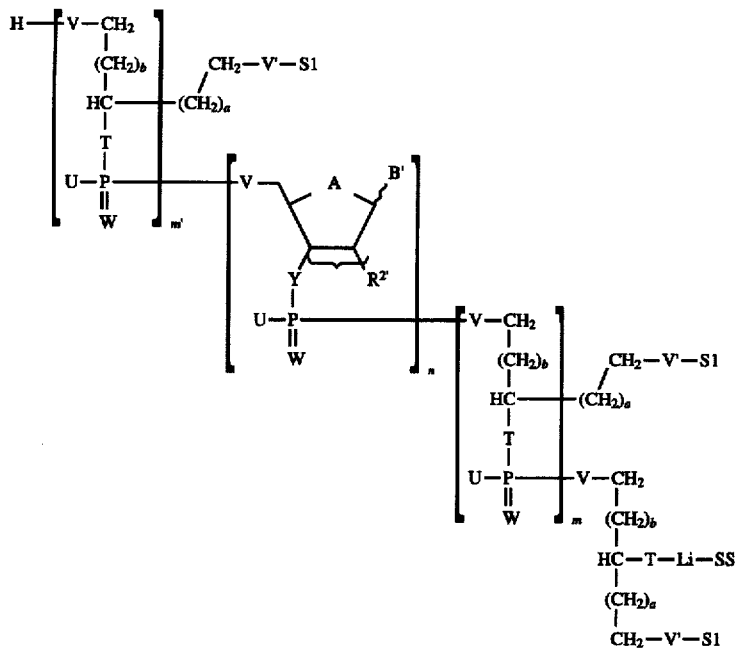

(XIII)

in which

A, B', Li, R²', S1, SS, T, U, V, V', W, Y, a, b, m, m' and n are as defined above;

h) if m' is 0 and n' is 1–50, carrying out reaction step f), which is then repeated (n'-1) times where appropriate, resulting in the compounds of the formula XIV in which A, B', Li, R²', S1, SS, T, U, V, V', W, Y, a, b, m, m', n and n' are as defined above;

i) where appropriate if R¹≠H in formula I, introducing the radical R¹ by known processes into the compound obtained in f), g) or h), preferably by appropriate reaction analogous

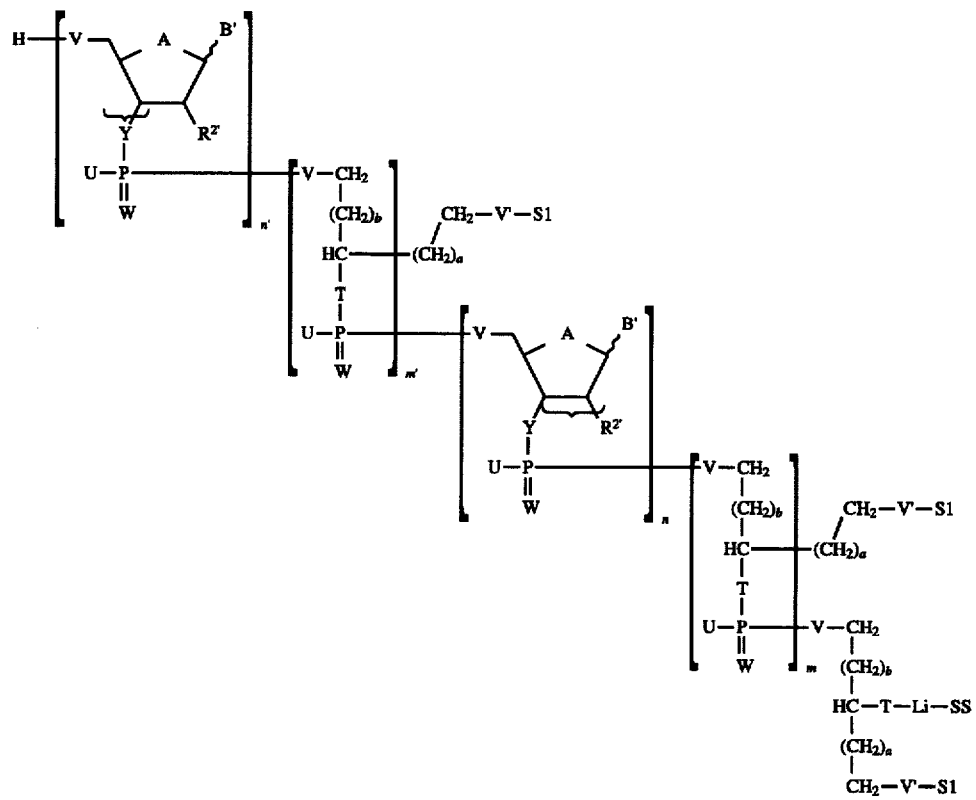

(XIV)

to reaction steps l) and m), where $R^1$ are $C_1$–$C_{18}$-alkyl, preferably $C_1$–$C_6$-alkyl, in particular methyl, $C_2$–$C_{18}$-alkenyl, $C_3$–$C_{18}$-alkynyl, $C_1$–$C_{18}$-alkylcarbonyl, $C_2$–$C_{19}$-alkenylcarbonyl, $C_3$–$C_{19}$-alkynylcarbonyl, $C_6$–$C_{20}$-aryl, $C_6$–$C_{14}$-aryl-$C_1$–$C_8$-alkyl, or a radical of the formula III

(III)

in which

W, Z and Z' are as defined above, preferably a radical of the formula III;

j) if $R^1$=H in formula I, capping by known methods, for example by reaction with acetic anhydride and N-methylimidazole;

f) if $R^1$=H in formula II, capping by known methods, for example by reaction with acetic anhydride and N-methylimidazole;

k) subsequently eliminating the protective group S1 by known processes (for example Greene, Wuts, "Protective Groups in Organic Synthesis", J. Wiley, New York 1991) from the oligonucleotides which are obtained in this way and are still linked to the support and protected, so that the linker to the solid support and the other protective groups present in the molecule are retained, for example for S1=levuloyl by treatment with hydrazine and for S1=paramethoxyphenyl preferably by treatment with the $Ce^{IV}$, for example with a 0.05–1M solution of $Ce^{IV}(NH_4)_2(NO_3)_6$ in acetonitrile/$H_2O$ at –10° to 100° C. for 0.2 to 500 minutes, preferably with a 0.05 to 0.5M, in particular 0.1M, solution of $Ce^{IV}(NH_4)_2(NO_3)_6$ in acetonitrile/$H_2O$ (2:1 to 8:1, in particular 4:1) at 0°–50° C., in particular 20°–30° C., for 1–30 min, in particular for 2 to 10 min;

l) and reacting the compound obtained in this way with a compound of the formula XV

(XV)

in which $R^9$, $R^{10}$, $R^{12}$ have the abovementioned meanings, and

Z" has the meaning of g as defined above or else is Z protected by known processes, the protective groups which are preferably used being those eliminated under conditions used for the elimination of protective groups in the oligonucleotide synthesis, examples which may be mentioned being hydroxyl, mercapto and SeH, which must be in the form of protected derivatives, for example as —O—CH$_2$—CH$_2$—CN, O—CH$_3$, S—CH$_2$—CH$_2$—CN or

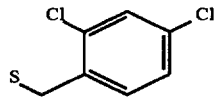

in the presence of a compound of the formula [HNR$^{14}$R$^{15}$R$^{16}$]$^{(+)}$E$^{(-)}$, where R$^{14}$, R$^{15}$, R$^{16}$ and E are as defined above, or in the presence of tetrazole or substituted tetrazole, such as, for example, 5-(4-nitrophenyl)-1H-tetrazole or 5-methylthio-1H-tetrazole or 5-ethylthio-1H-tetrazole, preferably in the presence of substituted tetrazole, such as, for example, 5-(4-nitrophenyl)-1H-tetrazole or 5-methylthio-1H-tetrazole or 5-ethylthio-1H-tetrazole, particularly preferably in the presence of 5-methylthio-1H-tetrazole, in a suitable organic solvent, preferably acetonitrile;

m) oxidizing the resulting compound by known processes, for example by reaction with iodine in the presence of aqueous pyridine, lutidine or collidine, where appropriate also in the presence of other organic solvents such as, for example, tetrahydrofuran, or, for example, by reaction with N,N,N',N'-tetraethylthiuram disulfide in acetonitrile, or, for example, by reaction with iodine in the presence of alkylamine or arylamine, the various oxidation processes which are known to the skilled worker and are used to prepare natural and modified oligonucleotides being summarized, for example, in Beaucage and Iyer, Tetrahedron 49 (1993) 1925 & 2223 & 6123; E. Sonveaux, Bioorg. Chem. 14 (1986) 274 and E. Uhlmann and A. Peyman, Chemical Reviews 90 (1990) 543, and the oxidation preferably being carried out by reaction with iodine in the presence of aqueous pyridine, lutidine or collidine, where appropriate also in the presence of other organic solvents such as tetrahydrofuran;

n) eliminating the oligonucleotide from the support by known processes, for example with NH$_3$ at 50°–60° C., and eliminating the remaining protective groups on the phosphate and nucleotide bases likewise by known processes.

The process for the preparation of compounds of the formula II comprises a) eliminating in a compound of the formula XVI

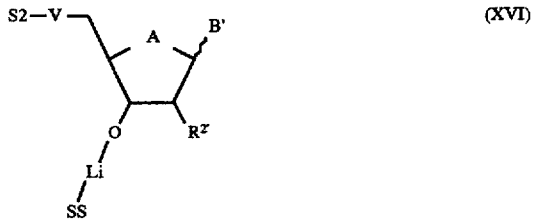
(XVI)

in which

A, B', Li, R$^{2'}$, S2, SS and V are as defined above, and Li can additionally be a linker which permits introduction of 3'-phosphate residue (see, for example, EP-A 0 552 766, Beaucage and Iyer, Tetrahedron 49 (1993) 2223 & 6123), the protective group S2 by known processes, for example by treatment with 1–4% dichloroacetic acid (DCA) in dichloromethane or chloroform;

b) subsequently reacting the resulting compound by the phosphoramidite method (E. Sonveaux, Bioorg. Chem. 14 (1986) 274) with a nucleoside phosphoramidite of the formula XI

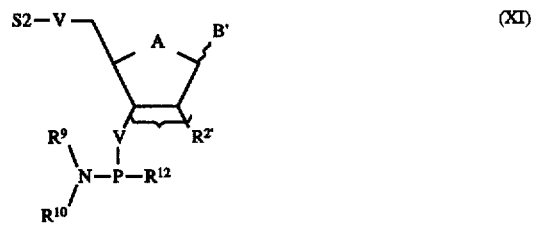
(XI)

in which

B' is defined as B and R$^{2'}$ is defined as R$^2$, and these can also be in protected form where appropriate, for example R$^2$ can be hydroxyl protected by tert-butyldimethylsilyl, and R$^9$, R$^{10}$, R$^{12}$, S2 and V are as defined above, oxidizing the resulting compound by known processes, carrying out a capping in the conventional way, eliminating the protective group S2, preferably dimethoxytrityl or monomethoxytrityl, by known processes (for example Beaucage and Iyer, Tetrahedron 49 (1993) 1925 & 2223 & 6123; E. Sonveaux, Bioorg. Chem. 14 (1986) 274; E. Uhlmann and A. Peyman, Chemical Reviews 90 (1990) 543), and then repeating this reaction step (n-1) times where appropriate, resulting in a compound of the formula XVII

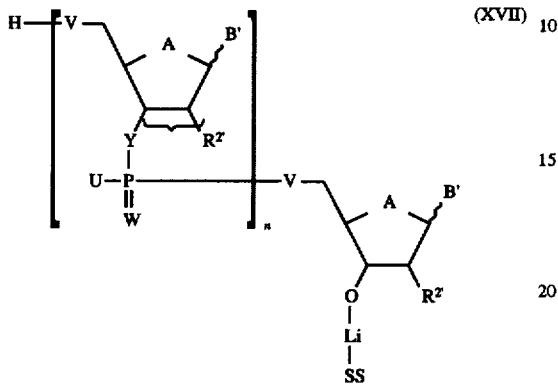

(XVII)

in which

A, B', Li, $R^{2'}$, SS, U, V, W, Y and n are as defined above;

c) subsequently reacting the resulting compound with a compound of the formula IX

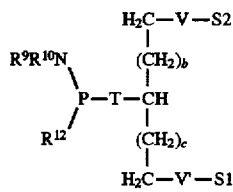

(IX)

in which

S1, S2, V, V', T, a and b are as defined above and $R^9$ and $R^{10}$ are identical or different and are $C_1$–$C_8$-alkyl, preferably isopropyl, or $C_5$–$C_{12}$-cycloalkyl, preferably up to $C_8$, benzyl or phenyl or together with the nitrogen atom to which they are bonded a saturated or unsaturated heterocyclic ring, optionally with further hereto atoms, such as, for example, morpholine, and substituents such as OC(O)O—$C_1$–$C_4$-alkyl esters, $R^{12}$ is $OR^{13}$ or $C_1$–$C_{18}$-alkyl, $C_1$–$C_{18}$-alkoxy, $C_6$–$C_{20}$-aryl, $C_6$–$C_{14}$-aryl-$C_1$–$C_8$-alkyl, preferably $OR^{13}$, $C_1$–$C_6$-alkyl, $C_1$–$C_6$-alkoxy, $C_6$–$C_{20}$-aryl, $C_6$–$C_{14}$-aryl-$C_1$–$C_8$-alkyl, particularly preferably $OR^{13}$ or $C_1$–$C_6$-alkyl, $R^{13'}$ is a group of the formula

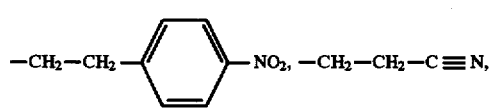

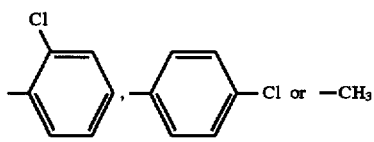

or a benzyl group, which is not or is one to four times ring-substituted, preferably not substituted, where the substituent or substituents is, independently of one another, fluorine, chlorine, bromine, a $C_1$–$C_4$-alkyl, nitro, methoxy or carboxyl group, in the presence of a compound of the formula $[HNR^{14}R^{15}R^{16}]^{(+)}E^{(-)}$, where $R^{14}$, $R^{15}$ and $R^{16}$ are identical to or different from one another and are a $C_1$–$C_4$-alkyl group and E is fluorine, chlorine, bromine, in particular chlorine, or in the presence of tetrazole or substituted tetrazole, such as, for example, 5-(4-nitrophenyl)-1H-tetrazole or 5-methylthio-1H-tetrazole or 5-ethylthio-1H-tetrazole, preferably in the presence of substituted tetrazole such as, for example, 5-(4-nitrophenyl)-1H-tetrazole or 5-methylthio-1H-tetrazole or 5-ethylthio-1H-tetrazole, particularly preferably in the presence of 5-methylthio-1H-tetrazole, in a suitable organic solvent, preferably acetonitrile, oxidizing the resulting compound by known processes, for example as described in reaction step m), carrying out a capping in the conventional way, eliminating the protective group S2 (for example Beaucage and Iyer Tetrahedron 49 (1993) 1925 & 2223 & 6123; E. Sonveaux, Bioorg. Chem. 14 (1986) 274; E. Uhlmann and A. Peyman, Chemical Reviews 90 (1990) 543)

and, where appropriate, then repeating this reaction step (m'-1) times, resulting in a compound of the formula XVIII

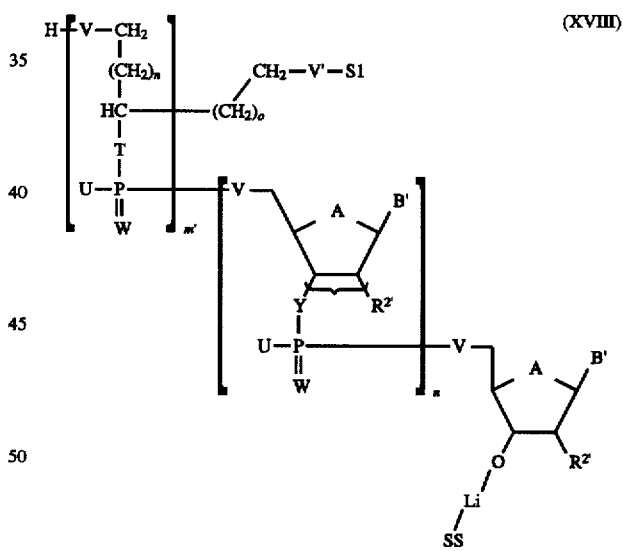

(XVIII)

in which

A, B', Li, $R^{2'}$, S1, SS, U, V, V', W, Y, a, b, m' and n are as defined above;

d) if n' is 1–50, carrying out reaction step b), which is repeated (n'-1) times where appropriate, resulting in the compound of the formula XIX

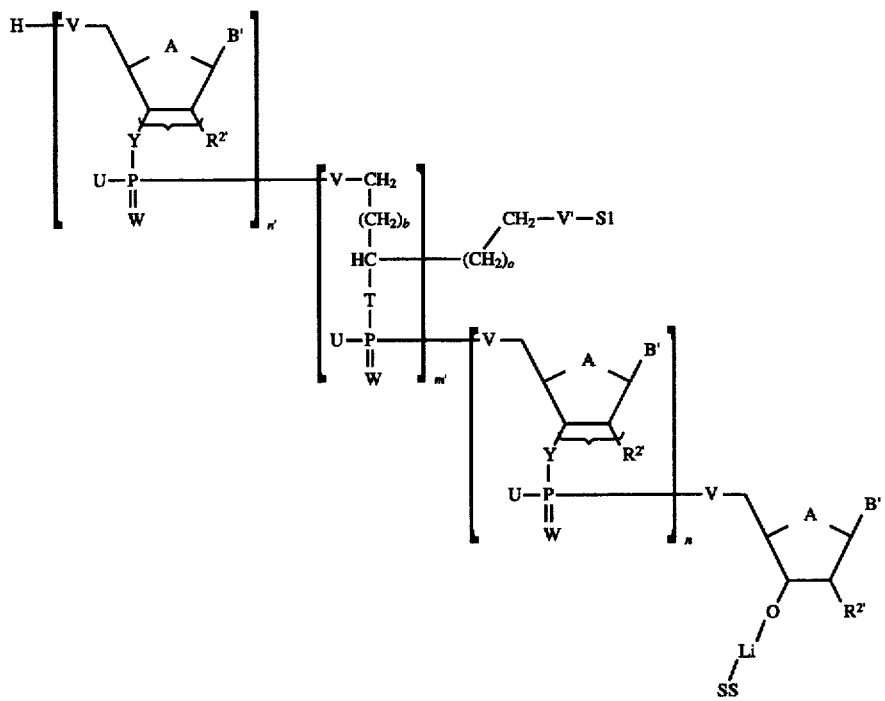

(XIX)

in which A, B', Li, $R^{2'}$, S1, SS, U, V, V', W, Y, a, b, m', n and n' are as defined above;

e) where appropriate if $R^1 \neq H$ in formula II, introducing the radical $R^1$ by known processes into the compound obtained in c) or d), preferably by appropriate reaction analogous to reaction steps h) and i), where $R^1$ is $C_1$–$C_{18}$-alkyl, preferably $C_1$–$C_6$-alkyl, in particular methyl, $C_2$–$C_{18}$-alkenyl, $C_3$–$C_{18}$-alkynyl, $C_1$–$C_{18}$-alkylcarbonyl, $C_2$–$C_{19}$-alkenylcarbonyl, $C_3$–$C_{19}$-alkynylcarbonyl, $C_6$–$C_{20}$-aryl, $C_6$–$C_{14}$-aryl-$C_1$–$C_8$-alkyl, or a radical of the formula III

(III)

in which

W, Z and Z' are as defined above, preferably a radical of the formula III;

f) if $R^1$=H in formula II, capping by known methods, for example by reaction with acetic anhydride and N-methylimidazole;

g) subsequently eliminating the protective group S1 by known processes (for example Greene, Wuts, "Protective Groups in Organic Synthesis", J. Wiley, New York 1991) from the oligonucleotides which are obtained in this way and are still linked to the support and protected, so that the linker to the solid support and the other protective groups present in the molecule are retained, for example for S1=levuloyl by treatment with hydrazine and for S1=para-methoxyphenyl preferably by treatment with the $Ce^{IV}$, for example with a 0.05–1M solution of $Ce^{IV}(NH_4)_2(NO_3)_6$ in acetonitrile/$H_2O$ at −10° to 100° C. for 0.2 to 500 minutes, preferably with a 0.05 to 0.5M, in particular 0.1M, solution of $Ce^{IV}(NH_4)_2(NO_3)_6$ in acetonitrile/$H_2O$ (2:1 to 8:1, in particular 4:1) at 0°–50° C., in particular 20°–30° C., for 1-30 min, in particular for 2 to 10 min;

h) and reacting the compound obtained in this way with a compound of the formula XV

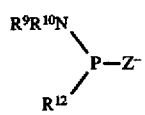

(XV)

in which $R^9$, $R^{10}$, $R^{12}$ have the abovementioned meanings, and

Z" has the meaning of Z as defined above or else is Z protected by known processes, protective groups which are preferably used being those eliminated under conditions used for the elimination of protective groups in the oligonucleotide synthesis, examples which may be mentioned being hydroxyl, mercapto and SeH, which must be in the form of protected derivatives, for example as O—$CH_2CH_2$–CN, O—$CH_3$, S—$CH_2$—$CH_2$—CH or

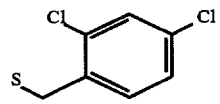

in the presence of a compound of the formula $[HNR^{14}R^{15}R^{16}]^{(+)}E^{(-)}$, where $R^{14}$, $R^{15}$, $R^{16}$ and E are as defined above, or in the presence of tetrazole or substituted tetrazole, such as, for example, 5-(4-nitrophenyl)-1H-tetrazole or 5-methylthio-1H-tetrazole or 5-ethylthio-1H-tetrazole, preferably in the presence of tetrazole or substituted tetrazole, such as, for example, 5-(4-nitrophenyl)-1H-tetrazole or 5-methylthio-1H-tetrazole or 5-ethylthio-1H-tetrazole, particularly preferably in the presence of 5-methylthio-1H-tetrazole, in a suitable organic solvent, preferably acetonitrile;

i) oxidizing the resulting compound by known processes, for example by reaction with iodine in the presence of aqueous pyridine, luridins or collidine, where appropriate also in the presence of other organic solvents such as, for example, tetrahydrofuran, or, for example, by reaction with N,N,N',N'-tetraethylthiuram disulfide in acetonitrile, or, for example, by reaction with iodine in the presence of alkylamine or arylamine, the various oxidation processes which are known to the skilled worker and are used to prepare natural and modified oligonucleotides being summarized, for example, in Beaucage and Iyer, Tetrahedron 49 (1993) 1925 & 2223 & 6123; E. Sonveaux, Bioorg. Chem. 14 (1986) 274 and E. Uhlmann and A. Peyman, Chemical Reviews 90 (1990) 543, and the oxidation preferably being carried out by reaction with iodine in the presence of aqueous pyridine, lutidine or collidine, where appropriate also in the presence of other organic solvents such as tetrahydrofuran;

j) eliminating the oligonucleotide from the support by known processes, for example with $NH_3$ at 50°–60° C., and eliminating the remaining protective groups on the phosphate and nucleotide bases likewise by known processes.

The nature of the amino protective groups on the bases and the properties of the linker Li depend in the individual case on the nature of the substituent Z because it must be possible to eliminate the latter without problems after the synthesis is complete. For example, in the preparation of an isopropyl oligonucleotide-3'-phosphate (Z=O-i-$CH_3H_7$) it is possible to use as protective groups benzoyl (Bz) for B=Ade and Cyt and isobutyryl (i-Bu) for B=Gua. On the other hand, to synthesize an oligonucleotide-3'-methylphosphonate (Z=$CH_3$) or ethyl ester (Z=O—$C_2H_5$) the protective groups used are preferably the more labile phenoxyacetyl (PAC) for B=Ade and Gua and isobutyryl for B=Cyt.

The compounds of the formula IX

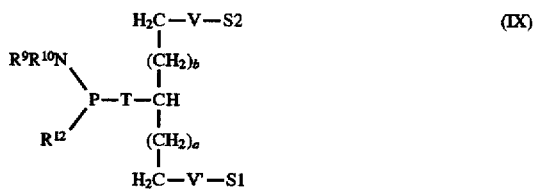

(IX)

in which

S1, S2, V, V', T, a and b are as defined above, and $R^9$ and $R^{10}$ are identical or different and are $C_1$–$C_8$-alkyl, preferably isopropyl, or $C_5$–$C_{12}$-cycloalkyl, preferably up to $C_8$, benzyl or phenyl or together with the nitrogen atom to which they are bonded a saturated or unsaturated heterocyclic ring, optionally with further hetero atoms, such as, for example, morpholine, and substituents such as OC(O)O—$C_1$–$C_4$-alkyl esters, $R^{12}$ is $OR^{13}$ or $C_1$–$C_{18}$-alkyl, $C_1$–$C_{18}$-alkoxy, $C_6$–$C_{20}$-aryl, $C_6$–$C_{14}$-aryl-$C_1$–$C_8$-alkyl, preferably $OR^{13}$, $C_1$–$C_6$-alkyl, $C_1$–$C_6$-alkoxy, $C_6$–$C_{20}$-aryl, $C_6$–$C_{14}$-aryl-$C_1$–$C_8$-alkyl, particularly preferably $OR^{13}$ or $C_1$–$C_6$-alkyl, $R^{13}$ is a group of the formula

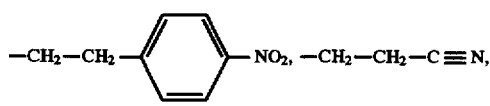

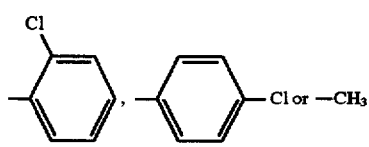

or a benzyl group, which is not or is one to four times ring-substituted, preferably not substituted, where the substituent or substituents is, independently of one another, fluorine, chlorine, bromine, a $C_1$–$C_4$-alkyl, nitro, methoxy or carboxyl group, can be obtained by reacting a compound of the formula VI

(VI)

with a compound of the formula XX

(XX)

in which $R^9$, $R^{10}$ and $R^{12}$ are as defined above, and $R^{11}$ is chlorine or bromine or a radical of the formula $NR^9R^{10}$, where $R^9$ and $R^{10}$ are as defined above;

in the presence of a base, preferably pyridine, or of a mixture of tetrahydrofuran (THF), dioxane, dichloromethane (DCM), chloroform and/or acetonitrile with a $C_1$–$C_4$-trialkylamine, preferably trimethyl-, triethyl- or diisopropylethylamine, or, if $R^{11}$ is a radical of the formula $NR^9R^{10}$, then in the presence of a compound of the formula $[HNR^{14}R^{15}R^{16}]^{(+)}E^{(-)}$ where $R^{14}$, $R^{15}$, $R^{16}$ are identical to or different from one another and are a $C_1$–$C_4$-alkyl group and E is fluorine, chlorine, bromine, in particular chlorine, or in the presence of tetrazole or substituted tetrazole such as, for example, 5-(4-nitrophenyl)-1H-tetrazole or 5-methylthio-1H-tetrazole or 5-ethylthio-1H-tetrazole, preferably in the presence of tetrazole.

In place of the phosphoramidite method, it is also possible to obtain the compounds of the formulae I and II by solid-phase synthesis by the H-phosphonate method or the phosphotriester method (E. Uhlmann and A. Peyman, Chemical Reviews 90 (1990) 543).

When the H-phosphonate method is used, the compound of the formula VI obtained after reaction step a) (preparation of compounds of the formula I) is converted by known processes (for example B. Froehler, Tetrahedron Lett. 27 (1986) 5575) into a compound of the formula XXI

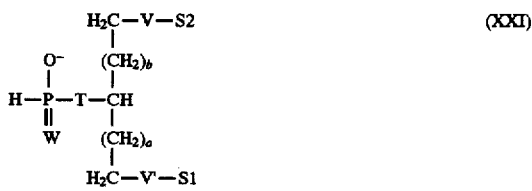

(XXI)

in which V, V', T, a, b and W have the abovementioned meaning. An example which may be mentioned is the reaction with

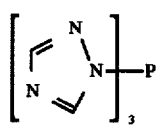

in a suitable organic solvent, for example dichloromethane, and subsequent hydrolysis. On introduction of the group Z (reaction step i) for compounds of the formula I and reaction step e) for compounds of the formula II) in the H-phosphonate method there is reaction with a compound of the formula XXII

in which Z" and W have the abovementioned meanings, in the presence of a condensing agent such as pivaloyl or adamantoyl chloride, and of a base such as pyridine. The H-phosphonate diester which is formed is then subjected to an oxidative phosphoramidation (B. Froehler, Tetrahedron Lett. 27, (1986) 5575) or an oxidation with iodine water, sulfur or selenium. It is possible in this way, for example, to prepare an oligonucleotide with a 3'-terminal cholesteryl group using cholesteryloxycarbonylaminoalkylamine in the presence of tetrachloromethane. Oxidative amidation with 2-methoxyethylamine results, for example, in oligonucleotides with a 3'—O-(2-methoxyethyl)phosphoramidate residue.

In the triester method, the compound of the formula VI obtained after reaction step a) (preparation of compounds of the formula I) is converted by known processes (for example Sonveaux, Bioorg. Chem. 14 (1986) 274) into a compound of the formula XXIII

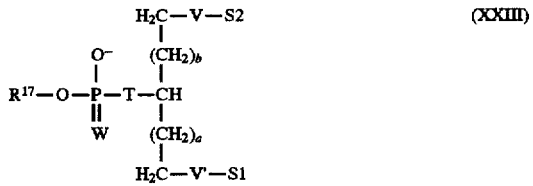

in which V, V', T, a, b and W have the abovementioned meaning, and $R^{17}$ is one of the protective groups used in the triester process and known to the skilled worker, for example 2,4-dichlorophenyl (E. Sonveaux, Bioorg. Chem. 14 (1986) 274). On introduction of the group Z (reaction step i) for compounds of the formula I and reaction step e) for compounds of the formula II) by the triester method there is reaction with a compound of the formula XXIV

in which Z, W and $R^{17}$ are as defined above, in the presence of a condensing agent. Preferred condensing reagents are arylsulfonyl chlorides such as mesitylene-, 2,4,6-triisopropylbenzene- or 8-quinolinesulfonyl chloride in the presence of nucleophilic catalysts such as imidazole, triazole or tetrazole or substituted derivatives thereof, such as N-methylimidazole, 3-nitrotriazole or 5-(p-nitrophenyl) tetrazole. Particularly preferred condensing agents are 4-substituted derivatives of pyridine N-oxide or quinoline N-oxide (Efimov et al., Nucleic Acids Research 13 (1985) 3651).

Oligonucleotide analogs of the formula I or of the formula II are used as inhibitors of gene expression.

The compounds of the present invention can be used, for example, as pharmaceuticals for the treatment of diseases caused by viruses (HIV, HSV-1, HSV-2, influenza, VSV, hepatitis B or papilloma viruses).

Antisense oligonucleotide sequences modified according to the invention and effective against such targets are, for example:

a) against HIV, for example
5'-ACACCCAATTCTGAAAATGG-3' SEQ ID NO: 1 (I) or
5'-AGGTCCCTGTTCGGGCGCCA-3' SEQ ID NO: 2 (II) or
5'-GTCGACACCCAATTCTGAAAATGGATAA-3' SEQ ID NO: 3 (III) or
5'-GCTATGTCGACACCCAATTCTGAAA-3' SEQ ID NO: 4 (IV) or
5'-TCGTCGCTGTCTCCGCTTCTTCTTCCTGCCA SEQ ID NO: 5 (V) or
5'-CTGTCTCCGCTTCTTCTTCCTGCCATAGGAG-3' SEQ ID NO: 6 (VI) or b) against HSV-1, for example
5'-GCGGGGCTCCATGGGGGTCG-3' SEQ ID NO: 7 (VII)

The compounds of the present invention are also suitable, for example, for the treatment of cancer. Examples of oligonucleotide sequences which can be used for this purpose are those directed against targets which are responsible for the development of cancer or growth of cancer. Pharmaceuticals of the present invention are furthermore suitable, for example, also for preventing restenosis. Examples of oligonucleotide sequences which can be used for this purpose are those directed against targets which are responsible for proliferation or migration. Examples of such targets are:

1) nuclear oncoproteins such as, for example, c-myc, N-myc, c-myb, c-fos, c-fos/Jun, PCNA, p120

2) cytoplasmic/membrane-associated oncoproteins such as, for example, Ej-ras, c-Ha-ras, N-ras, rrg, bcl-2, cdc-2, c-raf-1, c-mos, c-src, c-abl 3) cellular receptors, such as, for example, EGF receptor, FGF receptor, c-erbA, retinoid receptors, protein kinase regulatory subunit, c-fms, cdc2 kinase, 4) cytokines, growth factors, extracellular matrix, such as, for example, CSF-1, IL-6, IL-1a, IL-1b, IL-2, IL-4, bFGF, IGF, myeloblastin, fibronectin.

Antisense oligonucleotide sequences modified according to the invention and active against such targets are, for example a) against c-Ha-ras, for example
5'-CAGCTGCAACCCAGC-3' SEQ ID NO: 8 (VIII) or c) c-myc, for example
5'-GGCTGCTGGAGCGGGGCACAC-3' SEQ ID NO: 9 (IX) or
5'-AACGTTGAGGGGCAT-3' SEQ ID NO: 10 (X) or d) c-myb, for example
5'-GTGCCGGGGTCTTCGGGC-3' SEQ ID NO: 11 (XI) or e) c-fos, for example
5'-GGAGAACATCATGGTCGAAAG-3' SEQ ID NO: 12 (XII) or
5'-CCCGAGAACATCATGGTCGAAG-3' SEQ ID NO: 13 (XIII) or
5'-GGGGAAAGCCCGGCAAGGGG-3' SEQ ID NO: 14 (XIV) or f) p120, for example
5'-CACCCGCCTTGGCCTCCCAC-3; SEQ ID NO: 15 (XV) or g) EGF receptors, for example
5'-GGGACTCCGGCGCAGCGC-3' SEQ ID NO: 16 (XVI) or
5'-GGCAAACTTTCTTTTCCTCC-3' SEQ ID NO: 17 (XVII) or h) p53 tumor suppressor, for example
5'-GGGAAGGAGGAGGATGAGG-3' SEQ ID NO: 18 (XVIII) or
5'-GGCAGTCATCCAGCTTCGGAG-3' SEQ ID NO: 19 (XIX).

The compounds of the present invention are furthermore suitable, for example, for the treatment of disorders which are influenced by integrins or cell-cell adhesion receptors, for example by VLA-4, VLA-2, ICAM or ELAM.

Antisense oligonucleotide sequences modified according to the invention and active against such targets are, for example a) VLA-4, for example
5'-GCAGTAAGCATCCATATC-3' SEQ ID NO: 20 (XX) or b) ICAM, for example
5'-CCCCCACCACTTCCCCTCTC-3' SEQ ID NO: 21 (XXI) or
5'-CTCCCCCACCACTTCCCCTC-3' SEQ ID NO: 22 (XXII) or
5'-GCTGGGAGCCATAGCGAGG-3' SEQ ID NO: 23 (XXIII) or c) ELAM-1, for example
5'-ACTGCTGCCTCTTGTCTCAGG-3' SEQ ID NO: 24 (XXIV).

The oligonucleotide analogs of the formula I or of the formula II can furthermore be used as probe for detecting nucleic acids or as aids in molecular biology.

The invention furthermore relates to pharmaceutical compositions containing one or more oligonucleotide analogs of the formula I or II, where appropriate together with physiologically tolerated ancillary substances and/or vehicles and/or together with other known active substances, and to processes for the preparation thereof.

EXAMPLES

1) Synthesis of 4-methoxyphenyl 6-O-(4-methoxytriphenylmethyl)-β-O-succinylhexyl ether 1a) 2,2-Dimethyl-4-hydroxybutyl-1,3-dioxolane 15 g (112 mmol) of 1,2,6-hexanetriol were dissolved together with 0.5 g of $FeCl_3$ in 1 l of acetone and boiled under reflux for 7 h. The mixture was filtered, and excess acetone was removed by distillation, resulting in the product in pure form.

Yield: 18.8 g (96%);

$^1$H-NMR (200 MHz, $CDCl_3$/TMS): $d$=1.35 (s, 3H, $CH_3$); 1.40 (s, 3H, $CH_3$); 1.30–1.40 (m, 6H, —$(CH_2)_3$—); 3.52 (t, 1H, $C_4$—H); 3.68 (t, 2H, $CH_2$—OH); 4.00–4.20 (m, 2H, —$C^5H_2$—);

MS (EI): m/e=175 (M+H$^+$, 50%); 159 (30%)

1b) 4-Methoxyphenyl 4-(2,2-dimethyl-1,3-dioxolan-4-yl)-butyl ether 1.74 g (10 mmol) of 2,2-dimethyl-4-hydroxybutyl-1,3-dioxolane from Example 1a, 3.41 g (13 mmol) of triphenylphosphine, 2.26 g (13 mmol) of diethyl azodicarboxylate and 3.72 g (30 mmol) of 4-methoxyphenol were dissolved in 30 ml of absolute tetrahydrofuran (THF) and boiled under reflux for 1 h. The solvent was removed by distillation, and the residue was chromatographed on silica gel using ethyl acetate (EA)/n-heptane (1:4).

Yield: 2.1 g (74%);

$^1$H-NMR (200 MHz, $CDCl_3$/TMS): $d$=1.35 (s, 3H, $CH_3$); 1.41 (s, 3H, $CH_3$); 1.45–1.90 (m, 6H, —$(CH_2)_3$—); 3.53 (t, 1H, $C^4$—H); 3.77 (s, 3H, O—$CH_3$); 3.92 (t, 2H, $CH_2$—OAr); 3.99–4.21 (m, 2H, —$C^5H_2$—); 6.84 (s, 4H, Ar—H);

MS (EI): m/e=280 (M+H$^+$, 90%); 265 (50%); 223 (100%)

1c) 4-Methoxyphenyl 5,6-dihydroxyhexyl ether 2.08 g of 4-methoxyphenyl 4-(2,2-dimethyldioxolan-4-yl)butyl ether from Example 1b were dissolved in 165 ml of 80% acetic acid and stirred at room temperature for 4 h. The acetic acid was separated off in vacuo, and the mixture was then coevaporated with toluene/methanol twice. This resulted in a crystalline product.

Yield: 1.15 g (65%), mp: 69° C.

$^1$H-NMR (200 MHz, $CDCl_3$/TMS): $d$=1.40–1.91 (m, 6H, —$(CH_2)_3$—); 3.39–3.52 (m, 1H, $C^5$—H); 3.42–3.74 (m, 2H, $C^6H_2$) 3.77 (s 3H, O—$CH_3$); 3.93 (t, 2H, $CH_2$—OAr); 6.82 (s, 4H, Ar—H);

MS (EI): m/e=241 (M+H$^+$, 60%); 240 (M$^+$, 100%); 223 (30%), 205 (30%)

1d) 4-Methoxyphenyl 6-O-(4-methoxytriphenylmethyl)-5-hydroxyhexyl ether 1.96 g (8.2 mmol) of 4-methoxyphenyl 5,6-dihydroxyhexyl ether from Example 1c and 2.78 g (9.0 mmol) of 4-methoxytriphenylmethyl chloride were dissolved in 30 ml of absolute pyridine and stirred at room temperature for 3 h. The pyridine was evaporated off in vacuo, the residue was taken up in 40 ml of dichloromethane (DCM) and extracted first with 40 ml of 5% $NaHCO_3$ solution and then with 40 ml of saturated NaCl solution and washed twice with water. The solution was dried over sodium sulfate, the solvent was removed by distillation, and the residue was chromatographed on silica gel using EA/n-heptane (1:2).

Yield: 3.10 g (74%);

$^1$H-NMR (200 MHz, $CDCl_3$/TMS): $d$=1.37–1.80 (m, 6H, —$(CH_2)_3$—); 2.30 (d, J=5 Hz, 1H, $C^5$—H); 3.00–3.23 (m, 2H, $CH_2$—OMMTr); 3.73 (s, 3H, O—$CH_3$); 3.80 (s, 3H, O—$CH_3$); 3.88 (t, 2H, $CH_2$—OAr); 6.80 (s, 4H, Ar—H); 7.15–7.47 (m, 14H, Ar—H);

MS (ES$^+$, +LiCl): m/e=519 (M+Li$^+$, 100%)

1e) 4-Methoxyphenyl 6-O-(4-methoxytriphenylmethyl)-5-O-succinylhexyl ether 3.1 g (6.05 mmol) of 4-methoxyphenyl 6-O-(4-methoxytriphenylmethyl)-5-hydroxyhexyl ether from Example 1d were dissolved together with 0.85 g (8.47 mmol) of succinic anhydride and 1.04 g (8.47 mmol) of N,N-dimethylaminopyridine (DMAP) in 20 ml of absolute pyridine and stirred at room temperature for 19 h. The solvent was evaporated off in vacuo. It was then coevaporated twice with toluene/methanol, the residue was taken up in 280 ml of DCM and washed with 140 ml of 10% citric acid and twice with water and dried over sodium sulfate. The solvent was removed by distillation, and the residue was chromatographed on silica gel using EA/n-heptane 2:1.

Yield: 2.55 g (69%);

$^1$H-NMR (200 MHz, $CDCl_3$/TMS): $d$=1.27–1.49 (m, 2H, $C^2H_2$); 1.60–1.82 (m, 4H, $C^1H_2$ & $C^3H_2$); 2.66 (s, 4H, CO-$(CH_2)_2$-CO); 3.15 (d, 2H, $CH_2$—OMMTr); 3.75 (s, 3H, O—$CH_3$); 3.78 (s, 3H, O—$CH_3$); 3.89 (t, 2H, $CH_2$—OAr); 5.12 (dt, 1H, CH—Osucc); 6.80 (s, 4H, Ar—H); 7.11–7.52 (m, 14H, Ar—H);

MS (FAB+LiCl): m/e=625.3 (M+2Li$^+$—H$^+$, 100%); 619.2 (M+Li$^+$, 70%); 612.2 (M$^+$, 100%)

2) Synthesis of 4-methoxyphenyl 6-O-(4-methoxytriphenylmethyl)-5-O-diisopropylamino-β-cyanoethoxyphosphinohexyl ether 512 mg (1.0 mmol) of 4-methoxyphenyl 6-O-(4-methoxytriphenylmethyl)-5-hydroxyhexyl ether from Example 1d were coevaporated together with 390 mg (3.0 mmol) of diisopropylethylamine with absolute acetonitrile and then dissolved in 4 ml of absolute THF. Under protective gas, 330 mg (1.4 mmol) of cyanoethyl N,N-diisopropylchlorophosphoramidite were slowly added dropwise. The mixture was stirred at room temperature for 2 h. The solvent was evaporated off, and the residue was taken up in 20 ml of EA and extracted with 40 ml of saturated NaCl solution. The organic phase was then washed twice with water and subsequently dried over sodium sulfate. The solvent was removed by distillation, and the residue was chromatographed on silica gel using DCM/ethanol/triethylamine (TEA) (100:4:2).

Yield: 520 mg;

$^1$H-NMR (200 MHz, CDCl$_3$/TMS): d=1.00–1.93 (m, 18H, —(CH$_2$)$_3$— & 4×CH$_2$); 2.38 & 2.57 (each: t, 1H, CH$_2$—CN); 2.92–3.26 (m, 2H, P—O—CH$_2$); 3.45–4.20 (m, 13H, 2×OCH$_3$ & 2×CH(CH$_3$)$_2$ & CH$_2$—OAr & CH$_2$—O—MMTr & C$^5$H); 6.70–6.87 (s, 4H, Ar—H); 7.14–7.32 (m, 14H, Ar—H);

MS (FAB, LiCl; NBA): m/e=735.5 (M+Na$^+$, 100%); 719.5 (M+Li$^+$, 50%)

3) Synthesis of 4-methoxyphenyl 3-O-(4-methoxytriphenylmethyl)-2-O-succinylpropyl ether 3a) 4-Methoxyphenyl (2,2-dimethyl-1,3-dioxolan-4-yl)-methyl ether Synthesis took place in analogy to Example 1b from 2,2-dimethyl-4-hydroxymethyl-1,3-dioxolane.

Yield: 56%;

$^1$H-NMR (200 MHz, CDCl$_3$/TMS): d=1.40 (s, 3H, CH$_3$); 1.44 (s, 3H, CH$_3$); 3.78 (s, 3H, O—CH$_3$); 3.89 (dd, 2H, CH$_2$—OAr); 3.97–4.21 (m, 2H, —C$^3$H$_2$—); 4.45 (dt, 1H, C$_2$H); 6.83 (s, 4H, Ar—H);

MS (EI): m/e=239 (M+H$^+$, 40%); 238 (M$^+$, 50%)

3b) 4-Methoxyphenyl 2,3-dihydroxypropyl ether

Synthesis took place in analogy to Example 1c from 4-methoxyphenyl (2,2-dimethyl-1,3-dioxolan-4-yl)methyl ether (Example 3a).

Yield: 98%;

MS (EI): m/e=199 (M+H$^+$, 100%); 198 (M$^+$, 80%); 181 (40%); 163 (70%);

3c) 4-Methoxyphenyl 3-O-(4-methoxytriphenylmethyl)-2-hydroxypropyl ether

Synthesis took place in analogy to Example 1d from 4-methoxyphenyl 2,3-dihydroxypropyl ether (Example 3b).

Yield: 46%;

$^1$H-NMR (200 MHZ, CDCl$_3$/TMS): d=3.3.31 (d, 2H, CH$_2$—OMMTr); 3.77 (s, 3H, O—CH$_3$); 3.79 (s, 3H, O—CH$_3$); 3.96–4.20 (m, 3H, O—CH$_2$—CH); 6.76–6.90 (m, 4H, Ar—H); 7.15–7.55 (m, 14H, Ar—H);

MS (FAB+LiCl): m/e=477.2 (M+Li$^+$, 20%); 470.2 (M$^+$, 10%);

3d) 4-Methoxyphenyl 3-O-(4-methoxytriphenylmethyl)-2-O-succinylpropyl ether

Synthesis took place in analogy to Example 1e from 4-methoxyphenyl 3-O-(4-methoxytriphenylmethyl)-2-hydroxypropyl ether (Example 3c).

Yield: 98%;

$^1$H-NMR (200 MHz, CDCl$_3$/TMS): d=2.63 (s, 4H, CO-(CH$_2$)$_2$—CO); 3.31–3.40 (m, 2H, CH$_2$—OMMTr); 3.76 (s, 3H, O—CH$_3$); 3.79 (s, 3H, O—CH$_3$); 4.04–4.10 (m, 2H, CH$_2$—O—MOP); 5.35 (dt, 1H, CH—Osucc); 6.79 (s, 4H, Ar—H); 7.15–7.47 (m, 14H, Ar—H);

MS (FAB+LiCl): m/e=583.3 (M+2Li+—H$^+$, 40%); 577.3 (M+Li$^+$, 100%).

4) Synthesis of 6-O-(4-methoxytriphenylmethyl)-5-O-succinylhexyl levulinate 4a) 4-(2,2-Dimethyl-1,3-dioxolan-4-yl)butyl levulinate 0.81 g (5 mmol) of 2,2-dimethyl-4-hydroxybutyl-1,3-dioxolane from 1a were coevaporated twice with absolute acetonitrile, then dissolved together with 1.5 g (7 mmol) of levulinic anhydride and 0.86 g (7 mmol) of dimethylaminopyridine (DMAP) in absolute pyridine and stirred at room temperature for 15 h. The solvent was evaporated off in vacuo, and then three coevaporations with toluene were carried out. The residue was taken up in EA, and the organic phase was washed with saturated NaCl solution and with water and then dried over sodium sulfate. The solvent was evaporated off, and the residue was chromatographed on silica gel using EA.

Yield: 0.65 g (48%);

$^1$H-NMR (200 MHz, CDCl$_3$/TMS): d=1.37 (s, 3H, CH$_3$); 1.41 (s, 3H, CH$_3$); 1.42–1.75 (m, 6H, —(CH$_2$)$_3$—); 2.19 (s, 3H, CH$_3$—CO); 2.49–2.82 (m, 4H, COCH$_2$CH$_2$CO); 3.45–3.58 (m, 1H, C$^{4'}$—H); 3.97–4.16 (m, 4H, —C$^5$H$_2$— & CH$_2$—OCO);

MS (EI): m/e=273 (M+H$^+$, 45%); 257 (35%);

4b) 5,6-Dihydroxyhexyl levulinate

Synthesis took place in analogy to Example 1c from 4-(2,2-dimethyl-1,3-dioxolan-4-yl)butyl levulinate (Example 4a).

Yield: 90%;

$^1$H-NMR (200 MHz, CDCl$_3$/TMS): d=1.37–1.75 ( m, 6H, —(CH$_2$)$_2$—); 2.20 (s, 3H, CH$_3$—CO); 2.47–2.82 (m, 4H, COCH$_2$CH$_2$CO); 3.39–3.52 (dd, 1H, CH—OH); 3.60–3.79 (m, 2H, CH$_2$—OH); 4.11 (t, 2H, CH$_2$—OLev);

MS (EI): m/e=233 (M+H$^+$, 20%); 215 (15%);

4c) 6-O-( 4- Methoxytriphenylmethyl)-5-hydroxyhexyl levulinate

Synthesis took place in analogy to Example 1d from 5,6-dihydroxyhexyl levulinate (Example 4b) .

Yield: 40%;

$^1$H-NMR (200 MHz, CDCl$_3$/TMS): d=1.22–1.70 ( m, 6H, —(CH$_2$)$_3$—); 2.19 (s, 3H, CH$_3$—CO); 2.48–2.79 (m, 4H, COCH$_2$CH$_2$CO); 2.97–3.21 (m, 2H, CH$_2$—OMMTr); 3.79 (s, 3H, OCH$_3$); 3.68–3.82 (m, 1H, CH—OH); 4.03 (t, 2H, CH$_2$—OLev); 6.80–7.48 (m, Ar—H, 14H);

MS (ES$^+$+LiCl): m/e=511 (M+Li$^+$, 100%);

4d) 6-O-(4-methoxytriphenylmethyl)-5-O-succinylhexyl levulinate

Synthesis took place in analogy to Example 1e from 6-O-(4-methoxytriphenylmethyl)-5-hydroxyhexyl levulinate (Example 4c).

Yield: 80%;

$^1$H-NMR (200 MHz, CDCl$_3$/TMS): d=1.20–1.72 (m, 6H, —(CH$_2$)$_3$—); 2.19 (s, 3H, CH$_3$—CO); 2.49–2.80 (m, 8H, 2×COCH$_2$CH$_2$CO); 3.15 (d, 2H, CH$_2$—OMMTr); 3.79 (s, 3H, OCH$_3$); 4.03 (t, 2H, CH$_2$—OLev); 5.15 (m, 1H, CH—OSucc); 6.79–7.50 (m, Ar—H, 14H);

MS (ES$^+$+LiCl): m/e=627 (M+Na$^+$, 20%); 611 (M+Li$^+$, 50%).

5) Preparation of a support of the formula VIII-1 by loading aminopropyl-CPG with 4-methoxyphenyl 6-O-(4-methoxytriphenylmethyl)-5-O-succinylhexyl ether 123 mg (20 mmol) of 4-methoxyphenyl 6-O-(4-methoxytriphenylmethyl)-5-O-succinylhexyl ether (from Example 1) were coevaporated twice with absolute acetonitrile and then dissolved together with 7.1 mg (22 mmol) of O-(1-benzotriazolyl)-N,N,N',N'-tetramethyluroniumtetrafluoroborate (TBTU) and 3.2 mg (28 mmol) of N-ethylmorpholine in 0.75 ml of absolute dimethylformamide (DMF). 100 mg of aminopropyl-CPG (0.1 mmol/g, 550A) supplied by Fluka were added to this solution, and the suspension was shaken at room temperature for 7 h. The derivatized support was filtered off with suction, washed with methanol, DMF, THF, acetonitrile, again with methanol and with methylene chloride and dried at 40° C. in vacuo for 1 h. The loading of the support with monomethoxytrityl-containing component was 12.2 mmol/g. Reactive groups are capped in a DNA synthesizer using capping reagent (acetic anhydride/2,6-lutidine/1-methylimidazole; 0.25M each in THF), followed by washing with acetonitrile.

6) Preparation of a support of the formula VIII-2 by loading aminopropyl-CPG with 4-methoxyphenyl (2,2-dimethyl-1,3-dioxolan-4-yl)methyl ether Preparation in analogy to Example 5 using 4-methoxyphenyl (2,2-dimethyl-1,3-dioxolan-4-yl)methyl ether (from Example 3). The loading of the support with monomethoxytrityl-containing component was 36.7 mmol/g.

7) Preparation of a support of the formula VIII-3 by loading aminopropyl-CPG with 6-O-(4-methoxyphenylmethyl)-5-O-succinylhexyl levulinate Preparation in analogy to Example 5 using 6-O-(4-methoxytriphenylmethyl)-5-O-succinylhexyl levulinate (from Example 4). The loading of the support with monomethoxytrityl-containing component was 14.3 mmol/g.

8) Preparation of a support of the formula VIII-4 by loading ®Tentagel with 4-methoxyphenyl 6-O-(4-methoxytriphenylmethyl)-5-O-succinylhexyl ether 306 mg (0.5 mmol) of 4-methoxyphenyl 6-O-(4-methoxytriphenylmethyl)-5-O-succinylhexyl ether (from Example 1) were coevaporated twice with absolute acetonitrile and dissolved in a mixture of 1.25 ml of absolute THF and 65 ml of absolute pyridine. Then a solution of 70 mg (0.5 mmol) of 4-nitrophenol and 115 mg (0.55 mmol) of dicyclohexylcarbodiimide (DCC) in 0.35 ml of absolute THF was added, and the mixture was stirred at room temperature for 2 h. After the reaction was complete, the precipitated dicyclohexylurea was removed by centrifugation. The sediment was resuspended in 1 ml of ether and again centrifuged. 200 mg of ®Tentagel resin (PS/POE copolymer with 175 mmol/g amino functionality) were suspended in a mixture of 0.7 ml of absolute DMF and 0.14 ml of TEA, and the 4-nitrophenyl succinate solution obtained above was added, and the mixture was shaken at room temperature for 17 h. Filtration with suction was followed by working up as described in Example 5. The loading of the support with monomethoxytrityl-containing component was 28.7 mmol/g.

Oligonucleotide synthesis: the oligonucleotides are initially purified by butanol precipitation (Sawadogo, Van Dyke, Nucl. Acids Res. 19 (1991) 674). The sodium salt is then obtained by precipitation from a 0.5M NaCl solution with 2.5 parts by volume of ethanol.

The oligonucleotides are analyzed by a) analytical gel electrophoresis in 20% acrylamide, 8M urea, 454M tris-borate buffer, pH 7.0 and/or b) HPLC analysis: Waters GenPak FAX, gradient $CH_3CN$ (400 ml) $H_2O$ (1.6 l), $NaH_2PO_4$ (3.1 g), NaCl (11.7 g) pH 6.8 (0.1M in NaCl) to $CH_3CN$ (400 ml), $H_2O$ (1.6 l), $NaH_2PO_4$ (3.1 g), NaCl (175.3 g), pH 6.8 (1.5M in NaCl) and/or c) capillary gel electrophoresis, Beckmann eCAP™ capillary, U100P gel column, 65 cm length, 100 mm I.D., window 15 cm from one end, buffer 140 μM tris, 360 mM boric acid, 7M urea and/or d) electrospray mass spectroscopy.

9) Preparation of oligonucleotides of the formula I: TpTpTpTpTpTpTpTp—$CH_2$—$CH(OH)CH_2)_4$—(O-methoxyphenyl) SEQ ID NO: 25

The monomer is in each case a β-D-deoxyribonucleoside; $R^1=R^2=H$; Z=Q-(4-methoxyphenyl); n=8; m=m'=n'=b=0; A=V=W=U=X=Y=T=oxy; a=3;

a) 0.2 μmol of the support VIII-4 from Example 8 is treated successively with the following reagents:
1. absolute acetonitrile
2. 2.3% trichloroacetic acid in dichloromethane
3. absolute acetonitrile
4. 4 μmol of 5'-O-dimethoxytritylthymidine-3'-phosphorous acid β-cyanoethyl ester diisopropylamide and 25 μmol of tetrazole in 0.15 ml of absolute acetonitrile
5. acetonitrile
6. 20% acetic anhydride in THF with 40% lutidine and 10% dimethylaminopyridine
7. acetonitrile
8. iodine (0.1M $I_2$ in THF/water/pyridine; 70:20:5=v:v:v)

Steps 1 to 8, called one reaction cycle hereinafter, are repeated seven times to assemble the octathymidylate derivative.

b) After the synthesis is complete, the dimethoxytrityl group is eliminated as described in steps 1 to 3.

c) Treatment with ammonia for 1.5 hours cleaves the oligonucleotide off the support and simultaneously eliminates the β-cyanoethyl groups. Since the oligonucleotide contains no amino protective groups, no further ammonia treatment is necessary.

10) Preparation of oligonucleotides of the formula I: TpTpTpTpTpTpTpTp—$CH_2$—$CH(OH)CH_2)_4$—(OH) SEQ ID NO: 26

The monomer is in each case a β-D-deoxyribonucleoside; $R^1=R^2=H$; Z=OH; n=8, m=m'=n'=b=0; A=V=W=U=X=Y=T=Oxy; a=3;

a) Preparation takes place in analogy to Example 9a;

b) After the synthesis is complete, the dimethoxytrityl group (DMTr group) is eliminated as described in steps 1 to 3. Subsequently the 4-methoxyphenyl group (MOP group) is eliminated by treatment with 0.1M $Ce^{IV}(NH_4)_2(NO_3)_6$ in acetonitrile/$H_2O$ 4:1 at room temperature for 5 min.

c) Treatment with ammonia for 1.5 hours cleaves the oligonucleotide off the support and simultaneously eliminates the β-cyanoethyl groups.

11) Preparation of oligonucleotides of the formula I: TpTpTpTpTpTpTpTp—$CH_2$—$CN(OH)CH_2)_4$(O-($CH_2)_4$-pyrene) SEQ ID NO: 27 starting from support VIII-4

The monomer is in each case a β-D-deoxyribonucleoside; $R^1=R^2=H$; Z=O-(—($CH_2)_4$-pyrene); n=8, m=m'=n'=b=0; A=V=W=U=X=Y=T=Oxy; a=3;

a) Preparation takes place in analogy to Example 9a;

b) After the synthesis is complete, the dimethoxytrityl group is eliminated as described in steps 1 to 3. Subsequently the resulting free 5'-hydroxyl group is capped as described in steps 6 and 7. The 4-methoxyphenyl group is subsequently eliminated by treatment with 0.1M $Ce^{IV}(NH_4)_2(NO_3)_6$ in acetonitrile/$H_2O$ 4:1 at room temperature for 5 min.

c) Introduction of the 4-(1-pyrenyl)butyl phosphodiester at the 5' end takes place as described in J. S. Mann et al. Bioconj. Chem. 3 (1992) 554 by treatment with 4 μmol of 4-(1-pyrenyl)butyl 2-cyanoethyl N,N-diisopropylphosphoramidite and 25 μmol of methylthio-1H-tetrazole in 0.15 ml of absolute acetonitrile and subsequent washing with acetonitrile.

d) Oxidation with 0.1M $I_2$ in THF/water/pyridine; 70:20:5=v:v:v.

e) Treatment with ammonia for 1.5 hours cleaves the oligonucleotide off the support and simultaneously eliminates the β-cyanoethyl groups.

12) Preparation of oligonucleotides of the formula I: TpTpTpTpTpTpTpTp—$CH_2$—$CH(OH)CH_2)_4$—(O-($CH_2)_4$-pyrene) SEQ ID NO: 28 starting from support VIII-1

The monomer is in each case a β-D-deoxyribonucleoside; $R^1=R^2=H$; Z=O-(13 ($CH_2)_4$-pyrene); n=8, m=m'=n'=b=0; A=V=W=U=X=Y=T=Oxy; a=3;

Preparation takes place in analogy to Example 9a but using support VIII-1.

13) Preparation of oligonucleotides of the formula I: TpTpTpTpTpTpTpTp—CH'$_2$—$CH(OH)CH_2)_4$—(O-($CH_2)_{11}CH_3$) SEQ ID NO: 29 starting from support VIII-4

The monomer is in each case a β-D-deoxyribonucleoside; $R^1=R^2H$; $Z=O-(CH_2)_{11}CH_3$); n=8, m=m'=n'=0; A=V=W=U=X=Y=T=Oxy; a=3;

a) Preparation takes place in analogy to Example 9a;
b) Elimination of the DMTr group, capping and elimination of the MOP group as described in Example 11b;
c) Treatment with 4 μmol of dodecyl 2-cyanoethyl N,N-diisopropylphosphoramidite and 25 μmol of methylthio-1H-tetrazole in 0.15 ml of absolute acetonitrile and subsequent washing with acetonitrile.
d) Oxidation with 0.1M $I_2$ in THF/water/pyridine; 70:20:5=v:v:v.
e) Treatment with ammonia for 1.5 hours cleaves the oligonucleotide off the support and simultaneously eliminates the β-cyanoethyl groups.

14) Preparation of oligonucleotides of the formula I: TpTpTpTpTpTpTpTp—$CH_2$—$CN(OH)CH_2)_4$—(O-($CH_2$)$_{13}CH_3$) SEQ ID NO: 30 starting from support VIII-1

The monomer is in each case a β-D-deoxyribonucleoside; $R^1=R^2=H$; $Z=O-(CH_2)_{13}CH_3$); n=8, m=m'=n'=b=0; A=V=W=U=X=Y=T=oxy; a=3;

a) Preparation takes place in analogy to Example 9a;
b) Elimination of the DMTr group, capping and elimination of the MOP group as described in Example 11b;
c) Treatment with 4 μmol of tetradecyl 2-cyanoethyl N,N-diisopropylphosphoramidite and 25 μmol of methylthio-1H-tetrazole in 0.15 ml of absolute acetonitrile and subsequent washing with acetonitrile.
d) Oxidation with 0.1M $I_2$ in THF/water/pyridine; 70:20:5=v:v:v.
e) Treatment with ammonia for 1.5 hours cleaves the oligonucleotide off the support and simultaneously eliminates the β-cyanoethyl groups.

15) Preparation of oligonucleotides of the formula I: TpTpTpTpTpTpTpTp—$CH_2$—$CH(OH)CH_2$)—(O-3'—T—ODMtr) SEQ ID NO: 31 starting from support VIII-2

The monomer is in each case a β-D-deoxyribonucleoside; $R^1=R^2=H$; Z=O—3'—T—ODMTr; n=8, m=m'=n'=b=0; A=V=W=U=X=Y=T=oxy; a=0;

a) Preparation takes place in analogy to Example 9a;
b) Elimination of the DMTr group, capping and elimination of the MOP group as described in Example 11b;
c) Treatment with 4 μmol of 5'-O-dimethoxytritylthymidine-3'-phosphorous acid β-cyanoethyl ester diisopropylamide and 25 μmol of methylthio-1H-tetrazole in 0.15 ml of absolute acetonitrile and subsequent washing with acetonitrile.
d) Oxidation with 0.1M $I_2$ in THF/water/pyridine; 70:20:5=v:v:v.
e) Treatment with ammonia for 1.5 hours cleaves the oligonucleotide off the support and simultaneously eliminates the β-cyanoethyl groups.

16) Preparation of oligonucleotides of the formula I: TpTpTpTpTpTpTpTp—($CH_2$)4-$CH(OH)CH_2$)—(O-($CH_2$)$_{13}CH_3$) SEQ ID NO: 32 starting from support VIII-4

The monomer is in each case a β-D-deoxyribonucleoside; $R^1=R^2=H$; Z=O-(β-methoxyphenyl); n=8, m=m'=n'=a=0; A=V=W=U=X=Y=T=oxy; b=3;

a) 0.2 μmol of support VIII-4 from Example 8 are treated successively with the following reagents:
1. absolute acetonitrile
2. 3% trichloroacetic acid in dichloromethane
3. absolute acetonitrile
4. 4 μmol of tetradecyl 2-cyanoethyl N,N-diisopropylphosphoramidite and 25 μmol of methylthio-1H-tetrazole in 0.15 ml of absolute acetonitrile
5. acetonitrile
6. 0.1M $Ce^{IV}(NH_4)_2(NO_3)_6$ in acetonitrile/$H_2O$ 4:1 at room temperature for 5 min
7. acetonitrile
8. 4 μmol of 5'-O-dimethoxytritylthymidine-3'-phosphorous acid β-cyanoethyl ester diisopropylamide and 25 μmol of tetrazole in 0.15 ml of absolute acetonitrile
9. acetonitrile
10. 20% acetic anhydride in THF with 40% lutidine and 10% dimethylaminopyridine
11. acetonitrile
12. iodine (1.3 g in THF/water/pyridine; 70:20:5=v:v:v)
13. acetonitrile
14. 3% trichloroacetic acid in dichloromethane.

Steps 7-14, called one reaction cycle hereinafter, are repeated 7 times to assemble the octathymidylate derivative.
b) Treatment with ammonia at 60° C. for 12 hours cleaves the oligonucleotide off the support and simultaneously eliminates the β-cyanoethyl groups.

17) Preparation of oligouucleotides of the formula I: $G_pG_pA_pC_pC_pG_pA_pA_pG_pG_p$-($CH_2$)$_3$—CH(OH)—$CH_2$—(O-($CH_2$)$_{13}CH_3$) SEQ ID NO: 33 starting from support VIII-4

The monomer is in each case a β-D-deoxyribonucleoside; $R^1=R^2=H$; Z=O-(4-methoxyphenyl); n=10, m=m'=n'=a=0; A=V=W=U=X=Y=T=oxy; b=3;

Synthesis takes place in analogy to Example 16 but the relevant 3'-phosphorous acid β-cyanoethyl ester diisopropylamide of the appropriate base is used in step 8.

18) Preparation of oligonucleotides of the formula I: TpTpTpTpTpTpTpTp—($CH_2$)$_4$—$CH(OH)CH_2$)—(O-($CH_2$)$_{13}CH_3$) SEQ ID NO: 34 starting from support VIII-3

The monomer is in each case a β-D-deoxyribonucleoside; $R^1=R^2=H$; Z=O-(4-methoxyphenyl); n=8, m=m'=n'=a=0; A=V=W=U=X=Y=T=oxy; b=3;

Synthesis takes place in analogy to Example 16 but step 6 is replaced by treatment with 0.5M hydrazine hydrate in acetic acid/pyridine 2:3 for 30 min.

19) Preparation of oligonucleotides of the formula I: TpTpTpTpTpTpTpTp—$CH_2$—$CH(OH)CH_2$)$_4$—(O-acridin) SEQ ID NO: 35 starting from support VIII-4

The monomer is in each case a β-D-deoxyribonucleoside; $R^1=R^2=H$; Z=acridin; where acridin is 6-(2-methoxy-6-chloro-9-acridinylamino)-2-hydroxymethylhexoxy; n=8, m=m'=n'=b=0; A=V=W=U=X=Y=T=a=3;

a) Preparation takes place in analogy to Example 9a;
b) Elimination of the DMTr group, capping and elimination of the MOP group as described in 11b;
c) Treatment with 4 μmol of 6-(2-methoxy-6-chloro-9-acridinylamino)-2-dimethoxytrityloxymethyl-1-(2-cyanoethoxy-N,N-diisopropylaminophosphino)hexane (from Glen Research) and 25 μmol of methylthio-1H-tetrazole in 0.15 ml of absolute acetonitrile and subsequent washing with acetonitrile.
d) Oxidation with 0.1M $I_2$ in THF/water/pyridine; 70:20:5=v:v:v and washing with acetonitrile
e) Elimination of the DMTr group
f) Treatment with ammonia for 1.5 hours cleaves the oligonucleotide off the support and simultaneously eliminates the β-cyanoethyl groups.

20) Preparation of oligonucleotides of the formula I:

TpTpTpTpTpTpTpTp—$CH_2$—$CN(OH)CH_2$)$_4$-(O-biotin) SEQ ID NO: 36 starting from support VIII-4

The monomer is in each case a β-D-deoxyribonucleoside; $R^1=R^2=H$; Z=biotin; where biotin is 6-biotinamido-5-hydroxymethylhexoxy; n=8, m=m'=n'=b=0; A=V=W=U=X=Y=T=oxy; a=3;

a) Preparation takes place in analogy to Example 9a;

b) Elimination of the DMTr group, capping and elimination of the MOP group as described in 11b;

c) Treatment with 4 μmol of 6-biotinamido-5-dimethoxytrityloxymethylhexyl 2-cyanoethyl N,N-diisopropylphosphoramidite (from Glen Research) and 25 Aunol of methylthio-1H-tetrazole in 0.15 ml of absolute acetonitrile and subsequent washing with acetonitrile.

d) Oxidation with 0.1M $I_2$ in THF/water/pyridine; 70:20:5=v:v:v and washlag with acetonitrile e) Elimination of the DMTr group f) Treatment with ammonia for 1.5 hours cleaves the oligonucleotide off the support and simultaneously eliminates the β-cyanoethyl groups.

21) Preparation of oligonucleotides of the formula I: TpTpTpTpTpTpTpTp—$CH_2$—CN(OH)$CH_2)_4$-(O-TEGBiotin) SEQ ID NO: 37 starting from support VIII-4

The monomer is in each case a β-D-deoxyribonucleoside; $R^1=R^2=H$; Z=TEGBiotin; where TEGBiotin is 16-biotinamido-4,7,10,13-tetraoxy-1-hydroxy-2-hexadecoxy; n=8, m=m'=n'=b=0; A=V=W=U=X=Y=T=oxy; a=3;

a) Preparation takes place in analogy to Example 9a;

b) Elimination of the DMTr group, capping and elimination of the MOP group as described in 11b;

c) Treatment with 4 μmol of 16-biotinamido-4,7,10,13-tetraoxy-1-dimethyltrityloxy-2-hexadecyl 2-cyanoethyl N,N-diisopropylphosphoramidite (from Glen Research) and 25 μmol of methylthio-1H-tetrazole in 0.15 ml of absolute acetonitrile and subsequent washing with acetonitrile.

d) Oxidation with 0.1M $I_2$ in THF/water/pyridine; 70:20:5=v:v:v and washing with acetonitrile e) Elimination of the DMTr group f) Treatment with ammonia for 1.5 hours cleaves the oligonucleotide off the support and simultaneously eliminates the β-cyanoethyl groups.

22) Preparation of oligonucleotides of the formula I: TPTPTPTPTPTPTP—$CH_2$—CN(OH)$CH_2)_4$-(O-cholesterol) SEQ ID NO: 38 starting from support VIII-4

The monomer is in each case a β-D-deoxyribonucleoside; $R^1=R^2=H$; Z=cholesterol; where cholesterol is 16-cholesterylamino-4,7,10,13- tetraoxy-1-hydroxy-2-hexadecoxy; n=8, m=m'=n'=b=0; A=V=W=U=X=Y=T=oxy; a=3;

a) Preparation takes place in analogy to Example 9a;

b) Elimination of the DMTr group, capping and elimination of the MOP group as described in 11b;

c) Treatment with 4 μmol of 16-cholesterylamino-4,7,10,13-tetraoxy-1-dimethoxytrityloxy-2-hexadecyl 2-cyanoethyl N,N-diisopropylphosphoramidite (from Glen Research) and 25 μmol of methylthio-1H-tetrazole in 0.15 ml of absolute acetonitrile and subsequent washing with acetonitrile.

d) Oxidation with 0.1M $I_2$ in THF/water/pyridine; 70:20:5=v:v:v and washing with acetonitrile e) Elimination of the DMTr group f) Treatment with ammonia for 1.5 hours cleaves the oligonucleotide off the support and simultaneously eliminates the β-cyanoethyl groups.

23) Preparation of oligonucleotides of the formula I: TpTpTpTpTpTpTpTp—$CH_2$—CN(OH)$CH_2)_4$-(O-psoralen) SEQ ID NO: 39 starting from support VIII-4

The monomer is in each case a β-D-deoxyribonucleoside; $R^1=R^2=H$; Z=psoralen; where psoralen is 2-[4-(hydroxymethyl)-4,5',8-trimethylpsoralen]ethyl; n=8; m=m'=n'=b=0; A=V=W=U=X=Y=T=oxy; a=3;

a) Preparation takes place in analogy to Example 9a;

b) Elimination of the DMTr group, capping and elimination of the MOP group as described in 11b;

c) Treatment with 4 μmol of 2-[4-'(hydroxymethyl)-4,5', 8-trimethylpsoralen]ethyl 2-cyanoethyl N,N-diisopropylphosphoramidite (from Glen Research) and 25 μmol of methylthio-1H-tetrazole in 0.15 ml of absolute acetonitrile and subsequent washing with acetonitrile.

d) Oxidation with 0.1M $I_2$ in THF/water/pyridine; 70:20:5=v:v:v and washing with acetonitrile e) Treatment with ammonia for 1.5 hours cleaves the oligonucleotide off the support and simultaneously eliminates the β-cyanoethyl groups.

24) Preparation of oligonucleotides of the formula I: TpTpTpTpTpTpTpTp—$CH_2$—CN (OH)$CH_2$)—(O-($CH_2$)$_{13}CH_3$) SEQ ID NO: 40 starting from support VIII-2

The monomer is in each case a β-D-deoxyribonucleoside; $R^1=R^2=H$; Z=O-($CH_2)_{13}CH_3$; n=8, m=m'=n'=b=0; A=V=W=U=X=Y=T=oxy; a=0;

a) 0.2 μmol of support VIII-2 from Example 6 are treated successively with:

1. absolute acetonitrile
2. 3% trichloroacetic acid in dichloromethane
3. absolute acetonitrile
4. 4 μmol of tetradecyl 2-cyanoethyl N,N-diisopropylphosphoramidite and 25 μmol of methylthio-1H-tetrazole 0.15 ml of absolute acetonitrile
5. acetonitrile
6. 20% acetic anhydride in THF with 40% lutidine and 10% dimethylaminopyridine
7. acetonitrile
8. iodine (0.1M $I_2$ in THF/water/pyridine; 70:20:5=v:v:v)
9. 0.1M $Ce^{IV}(NH_4)_2(NO_3)_6$ in acetonitrile/HO 4:1 (see also Example 11b).
10. acetonitrile b) and subsequently treated with 1. 4 μmol of 5'-O-dimethoxytritylthymidine-3-phosphorous acid β-cyanoethyl ester diisopropylamide and 25 μmol of tetrazole in 0.15 ml of absolute acetonitrile
2. acetonitrile
3. 20% acetic anhydride in THF with 40% lutidine and 10% dimethylaminopyridine
4. acetonitrile
5. iodine (0.1M $I_2$ in THF/water/pyridine; 70:20:5 =v:v:v)
6. absolute acetonitrile
7. 3% trichloroacetic acid in dichloromethane
8. absolute acetonitrile.

Steps 1 to 8, hereinafter called one reaction cycle, are repeated 7 times to assemble the octathymidylate derivative.

c) Treatment with ammonia for 1.5 hours cleaves the oligonucleotide off the support and simultaneously eliminates the β-cyanoethyl groups. Since the oligonucleotide contains no amino protective groups, no further ammonia treatment is necessary.

25) Preparation of oligonucleotides of the formula I: CpApCpGpTpTpGpApGpGpGpGpGpCpApTp—$CH_2$—CH(OH)($CH_2$)—(O-($CH_2$)$_{13}CH_3$) SEQ ID NO: 41 starting from support VIII-2

The monomer is in each case a β-D-deoxyribonucleoside; $R^1=R^2=H$; Z=O-($CH_2)_{13}CH_3$; n=15, m=m'=n'=b=0; A=V=W=U=X=Y=T=oxy; a=0;

Synthesis in analogy to Example 24 but using the appropriate standard 5'-O-dimethoxytritylthymidine-protected 3'—(2-cyanoethyl)-N,N-diisopropylphosphoramidite nucleosides in step b1. Treatment with ammonia for 1.5 hours cleaves the oligonucleotide off the support, and deprotection took place by treatment with ammonia at 60° C. for 16 h.

26) Preparation of oligonucleotides of the formula I: CpApCpGpTpTpGpApGpGpGpGpCpApTp—CH$_2$—CH(OH)(CH$_2$)—(O-vitamin E) SEQ ID NO: 42 starting from support VIII-2

The monomer is in each case a β-D-deoxyrihonucleoside; $R^1=R^2=H$; Z=O-vitamin E; n=15, m=m'=n'=b=0; A=V=W=U=X=Y=T=oxy; a=0;

Synthesis in analogy to Example 24 but using the vitamin E2-cyanoethyl N,N-diisopropylphosphoramidite in step a4.

27) Synthesis of 3-O-(4-methoxytriphenylmethyl)-2-O-succinylpropyl levulinate 27a) (2,2-Dimethyl-1,3-dioxolan-4-yl) methyl levulinate Synthesis in analogy to Example 4a from 2,2-dimethyl-4-hydroxymethyl-1,3-dioxolane.

Yield: 71%.

$^1$H-NMR (200 MHz, CDCl$_3$/TMS): δ=1.38 (s, 3H, CH$_3$); 1.42 (s, 3H, CH$_3$); 2.19 (s, 3H, CH$_3$—CO); 2.51–2.82 (m, 4H, COCH$_2$CH$_2$CO); 3.75 (dd, 1H, C$^{4'}$—H); 4.01–4.39 (m, 4H, —C$^{5'}$H$_2$— & CH$_2$—OCO);

27b) 2,3-Dihydroxypropyl levulinate

Synthesis in analogy to 1c from (2,2-dimethyl-1,3-dioxolan-4-yl)methyl levulinate (27a);

Yield: 90%;

$^1$H-NMR (200 MHz, CDCl$_3$/TMS): δ=2.20 (s, 3H, CH$_3$—CO); 2.60, 2.80 (each t, 4H, COCH$_2$CH$_2$CO); 3.54–3.80 (m, 2H, CH$_2$—OH); 3.80 (t, 1H, OH); 3.95 (m, 1H, CH—OH); 4.21 (d, 2H, CH$_2$—OLev);

27c) 3-O-(4-Methoxytriphenylmethyl)-2-hydroxypropyl levulinate

Synthesis in analogy to 1d from 2,3-dihydroxypropyl levulinate (24b);

Yield: 20%;

27d) 3-O-(4-Methoxytriphenylmethyl)-2-O-succinylpropyl levulinate

Synthesis in analogy to 1e from 3-O-(4-methoxytriphenylmethyl)-2-hydroxypropyl levulinate (27c);

Yield: 51%;

MS (FAB/LiCl): m/e=599.3 (M+Li$^+$);

28) Preparation of a support of the formula VIII-5 by loading aminopropyl-CPG With 3-O-(4-methoxytriphenylmethyl)-2-O-succinylpropyl levulinate Preparation in analogy to Example 5 using 3-O-(4-methoxytriphenylmethyl)-2-O-succinylpropyl levulinate (from Example 27). The loading of the support with monomethoxytrityl-containing component was 24.7 μmol/g.

---

We claim:

1. A compound of the formula I or formula II

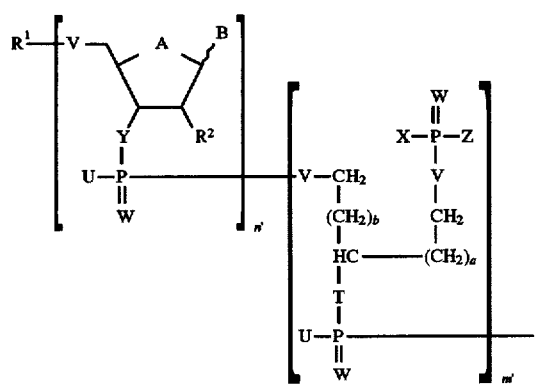

(I)

-continued

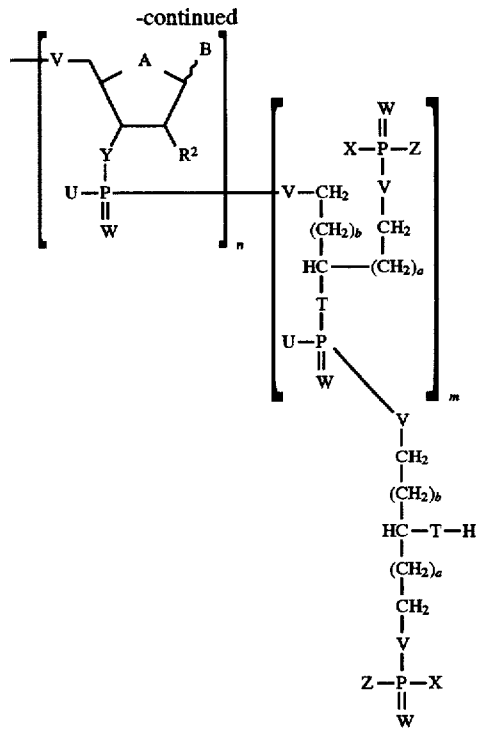

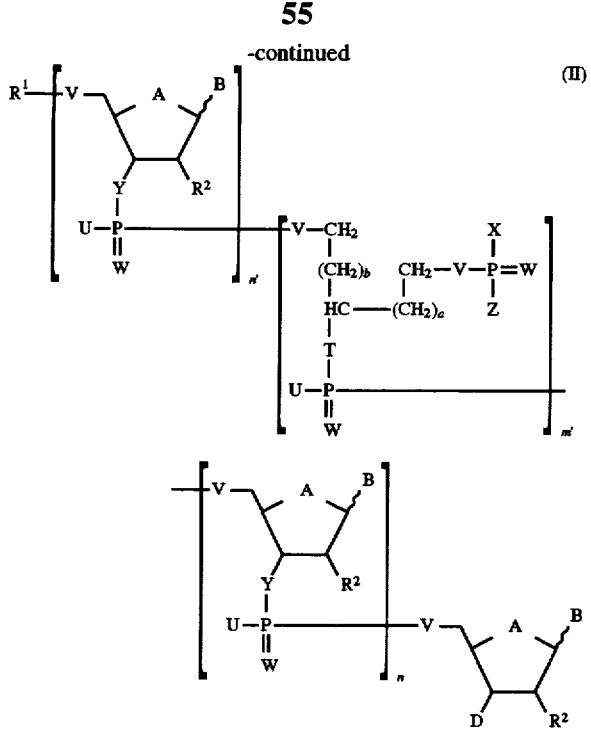

and the physiologically tolerated salts thereof, in which a is a number from zero to 20;

b is a number from zero to 20;

$R^1$ is hydrogen, $C_1$–$C_{18}$-alkyl, $C_2$–$C_{18}$-alkenyl, $C_3$–$C_{18}$-alkynyl, $C_1$–$C_{18}$-alkylcarbonyl, $C_2$–$C_{19}$-alkenylcarbonyl, $C_3$–$C_{19}$-alkynylcarbonyl, $C_6$–$C_{20}$-aryl, $C_6$–$C_{14}$-aryl-$C_1$–$C_8$-alkyl, or a radical of the formula III

(III)

$R^2$ is hydrogen, hydroxyl, $C_1$–$C_{18}$-alkoxy, halogen, azido or $NH_2$;

D is hydroxyl, O—$PO_3^{2-}$;

B is a base customary in nucleotide chemistry, for example natural bases or unnatural bases;

n is an integer from 1 to 100;

n' is an integer from zero to 50;

m is an integer from zero to 5;

m' in formula I is an integer from zero to 5;

m' in formula II is an integer from 1 to 5;

A is oxy, thioxy or methylene;

W is oxo, thioxo or selenoxo;

V is oxy or thio;

T is oxy, thio or imino;

Y is oxy, thio, imino or methylene;

X is hydroxyl or mercapto;

U is hydroxyl, mercapto, $BH_3$, SeH, $C_1$–$C_{18}$-alkoxy, $C_1$–$C_{18}$-alkyl, $C_6$–$C_{20}$-aryl, $C_6$–$C_{14}$-aryl-$C_1$–$C_8$-alkyl, $NHR^3$, $NR^3R^4$ or a radical of the formula IV

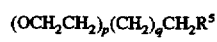
(IV)

in which $R^3$ is $C_1$–$C_{18}$-alkyl, $C_6$–$C_{20}$-aryl, $C_6$–$C_{14}$-aryl-$C_1$–$C_8$-alkyl, —$(CH_2)_c$—[$NH(CH_2)_c$]$_d$—$NR^6R^6$, in which c is an integer from 2 to 6 and d is an integer from zero to 6, and $R^6$ is, independently of one another, hydrogen, $C_1$–$C_6$-alkyl or $C_1$–$C_4$-alkoxy-$C_1$–$C_6$-alkyl;

$R^4$ is $C_1$–$C_{18}$-alkyl, $C_6$–$C_{20}$-aryl or $C_6$–$C_{10}$-aryl-$C_1$–$C_8$-alkyl, or, in the case of $NR^3R^4$, together with $R^3$ and the nitrogen atom carrying them is a 5–6-membered heterocyclic ring which can additionally contain another hetero atom from the series consisting of O, S and N;

p is an integer from 1 to 100;

q is an integer from zero to 22;

$R^5$ is hydrogen or a functional group such as hydroxyl, amino, $NHR^7$, COOH, $CONH_2$, $COOR^8$ or halogen, in which $R^7$ is $C_1$–$C_6$-alkyl and $R^8$ is $C_1$–$C_4$-alkyl;

Z, Z' are, independently of one another, hydroxyl, mercapto, SeH, $C_1$–$C_{22}$-alkoxy, —O—$(CH_2)_b$—$NR^7R^8$, in which b is an integer from 1 to 6, and $R^7$ is $C_1$–$C_6$-alkyl and $R^8$ is $C_1$–$C_4$-alkyl, or $R^7$ and $R^8$ form, together with the nitrogen atom carrying them, a 3–6-membered rings $C_1$–$C_{18}$-alkyl, preferably $C_1$–$C_8$-alkyl, $C_6$–$C_{20}$-aryl, $C_6$–$C_{14}$-aryl-$C_1$–$C_8$-alkyl, preferably $C_6$–$C_{10}$-aryl-$C_1$–$C_4$-alkyl, $C_6$–$C_{14}$-aryl alkoxy, preferably $C_6$–$C_{10}$-aryl-$C_1$–$C_4$-alkoxy, where aryl also means heteroaryl and aryl is optionally substituted by 1, 2 or 3 identical or different radicals from the series consisting of carboxyl, amino, nitro, $C_1$–$C_4$-alkylamino, $C_1$–$C_6$-alkoxy, hydroxyl, halogen and cyano, or $C_1$–$C_{18}$-alkylmercapto, $NHR^3$, $NR^3R^4$, in which $R^3$ and $R^4$ are as defined above, or a group which favors intracellular uptake or acts as labelling of a DNA probe or, on hybridization of the oligonucleotide analog onto to the target nucleic acid, interacts with the latter by binding, crosslinking or cleavage, or a nucleoside or oligonucleotide linked via the 5' or 3' ends; and the curved parenthesis indicates that $R^2$ and the adjacent phosphoryl radical can be located in the 2' and 3' positions or else conversely in the 3' and 2' positions, it being possible for each nucleotide to be in its D or L configuration and for the base B to be located in the α or β position.

2. A compound of the formula I or II as claimed in claim 1, and the physiologically tolerated salts thereof, wherein the base B is located in the β position, the nucleotides are in the D configuration, and $R^2$ is located in position 2'.

3. A compound of the formula I or II as claimed in claim 1 or 2, and the physiologically tolerated salts thereof, wherein a is a number from zero to 10;

b is a number from zero to 10;

$R^1$ is hydrogen or a radical of the formula III

(III)

$R^2$ is hydrogen or hydroxyl;

n is an integer from 5 to 40;

n' is an integer from zero to 30;

A is oxy;

W is oxo or thioxo;

U is hydroxyl, mercapto, $C_1$–$C_6$-alkoxy, $C_1$–$C_6$-alkyl, $NR^3R^4$ or $NHR^3$, in which $R^3$ is $C_1$–$C_{18}$-alkyl; and R⁴ is C₁-C₈-alkyl, C₆-C₂₀-aryl or C₆-C₁₀-aryl-C₁-C₈-alkyl or, in the case of NR³R⁴, together with R³ and the nitrogen atom carrying them is a 5–6-membered heterocyclic ring which can additionally contain another hetero atom from the series consisting of O, S, N.

4. A compound of the formula I or II as claimed in claim 1, and the physiologically tolerated salts thereof, wherein a is a number from zero to 4;
b is a number from zero;
R¹ is hydrogen;
R² is hydrogen;
D is hydroxyl;
B is adenine, cytosine, guanine, uracil, thymine, 5-propinuracil or 5-propincytosine;
n is an integer from 7 to 25;
n' is an integer from zero to 25;
m is zero;
m' in formula I is an integer from zero or 1;
m' in formula II is an integer from 1;
T is oxy;
Y is oxy;
U is hydroxyl or C₁-C₆-alkyl.

5. A compound of claim 1, wherein
R¹, R²=H;
Z=O-(4-methoxyphenyl);
n=8;
m, m', n', b=0;
A, V, W, U, X, Y, T=oxy; and
a=3.

6. A compound of claim 1, wherein
R¹, R²=H;
Z=OH;
n=8;
m, m', n', b=0;
A, V, W, U, X, Y, T=oxy; and
a=3.

7. A compound of claim 1, wherein
R¹, R²=H;
Z=O-(—(CH₂)₄-pyrene);
n=8;
m, m', n', b=0;
A, V, W, U, X, Y, T=oxy; and
a=3.

8. A compound of claim 1, wherein
R¹, R²=H;
Z=O-(≧(CH₂)₁₁—CH₃);
n=8;
m, m', n', b=0;
A, V, W, U, X, Y, T=oxy; and
a=3.

9. A compound of claim 1, wherein
R¹, R²=H;
Z=O—(—(CH₂)₁₃—CH₃);
n=8;
m, m', n', b=0;
A, V, W, U, X, Y, T=oxy; and
a=3.

10. A compound of claim 1, wherein
R¹, R²=H;

Z=O—3'—T—ODMtr;
n=8;
m, m', n', b=0;
A, V, W, U, X, Y, T=oxy; and
a=0.

11. A compound of claim 1, wherein
R¹, R²=H;
Z=O-(4-methoxyphenyl);
n=8;
m, m', n', a=0;
A, V, W, U, X, Y, T=oxy; and
b=3.

12. A compound of claim 1, wherein
R¹, R²=H;
Z=O-(4-methoxyphenyl);
n=10;
m, m', n', a=0;
A, V, W, U, X, Y, T=oxy; and
b=3.

13. A compound of claim 1, wherein
R¹, R²=H;
Z=O-(4-methoxyphenyl);
n=8;
m, m', n', a=0;
A, V, W, U, X, Y, T=oxy; and
b=3.

14. A compound of claim 1, wherein
R¹, R²=H;
Z=6-(2-methoxy-6-chloro-9-acridinylamino)-2-hydroxymethylhexoxy;
n=8;
m, m', n', b=0;
A, V, W, U, X, Y, T=oxy; and
a=3.

15. A compound of claim 1, wherein
R¹, R²=H;
Z=6-biotinamido-5-hydroxymethylhexoxy;
n=8;
m, m', n', b=0;
A, V, W, U, X, Y, T=oxy; and
a=3.

16. A compound of claim 1, wherein
R¹, R²=H;
Z=16-biotinamido-4,7,10,13-tetraoxy-1-hydroxy-2-hexadecoxy;
n=8;
m, m', n', b=0;
A, V, W, U, X, Y, T=oxy; and
a=3.

17. A compound of claim 1, wherein
R¹, R²=H;
Z=16-cholesterylamino-4,7,10,13-tetraoxy-1-hydroxy-2-hexadecoxy;
n=8;
m, m', n', b=0;
A, V, W, U, X, Y, T=oxy; and
a=3.

18. A compound of claim 1, wherein $R^1$, $R^2$=H;
Z=2-[4-'(hydroxymethyl)-4,5',8-trimethylpsoralen]ethyl;
m, m', n', b=0;
A, V, W, U, X, Y, T=oxy; and
a=3.

19. A compound of claim 1, wherein
$R^1$, $R^2$=H;
Z=O-(CH$_2$)$_{13}$CH$_3$;
n=8;
m, m', n', b=0;
A, V, W, U, X, Y, T=oxy; and
a=0.

20. A compound of claim 1, wherein
$R^1$, $R^2$=H;
Z=O-(CH$_2$)$_{13}$CH$_3$;
n=15;
m, m', n', b=0;
A, V, W, U, X, Y, T=oxy; and
a=0.

21. A compound of claim 1, wherein
$R^1$, $R^2$=H;
Z=O-vitamin E;
n=15;
m, m', n', b=0;
A, V, W, U, X, Y, T=oxy; and
a=0.

* * * * *

UNITED STATES PATENT AND TRADEMARK OFFICE
CERTIFICATE OF CORRECTION

PATENT NO. : 5,696,248
DATED : December 09, 1997
INVENTOR(S) : Anuschirwan PEYMAN et al.

It is certified that error appears in the above-indentified patent and that said Letters Patent is hereby corrected as shown below:

Claim 1, column 55, line 44, "O—$PO_3^{2-}$" should read --O—$PO_3^{2-}$--;

column 56, line 22, "rings" should read --ring--;

lines 33-34, "onto to the" should read --onto the--.

Claim 8, column 57, line 52, "($\geq(CH_2)_{11}$—$CH_3$)" should read --(-$(CH_2)_{11}$—$CH_3$)--.

Claim 10, column 58, line 1, "ODMtr" should read --ODMTr--.

Claim 18, column 59, line 3, before "m,m',n',b=0;" insert --n=8;--.

Signed and Sealed this

Twenty-first Day of July, 1998

Attest:

BRUCE LEHMAN

*Attesting Officer*        *Commissioner of Patents and Trademarks*